(12) United States Patent
Hirabayashi et al.

(10) Patent No.: US 8,822,667 B2
(45) Date of Patent: Sep. 2, 2014

(54) NUCLEIC ACID MOLECULE CAPABLE OF BINDING TO C-MET AND USE THEREOF

(75) Inventors: Naomi Hirabayashi, Yokohama (JP); Shotaro Tsuji, Yokohama (JP); Jou Akitomi, Koto-ku (JP); Shintarou Katou, Koto-ku (JP); Iwao Waga, Koto-ku (JP); Takashi Ohtsu, Yokohama (JP)

(73) Assignees: NEC Solution Innovators, Ltd., Tokyo (JP); Kanagawa Prefectural Hospital Organization, Kanagawa (JP)

( * ) Notice: Subject to any disclaimer, the term of this patent is extended or adjusted under 35 U.S.C. 154(b) by 0 days.

(21) Appl. No.: 13/812,190

(22) PCT Filed: Jul. 26, 2011

(86) PCT No.: PCT/JP2011/066962
§ 371 (c)(1),
(2), (4) Date: Jan. 25, 2013

(87) PCT Pub. No.: WO2012/014890
PCT Pub. Date: Feb. 2, 2012

(65) Prior Publication Data
US 2013/0123350 A1   May 16, 2013

(30) Foreign Application Priority Data

Jul. 26, 2010 (JP) .................................. 2010-167342

(51) Int. Cl.
*C07H 21/04* (2006.01)
*C07H 21/02* (2006.01)
*A61K 48/00* (2006.01)

(52) U.S. Cl.
USPC ............................. 536/24.5; 536/23.1; 514/44

(58) Field of Classification Search
CPC ........... G01N 2333/4753; G01N 33/74; C12N 2310/321; C12N 15/115
See application file for complete search history.

(56) References Cited

U.S. PATENT DOCUMENTS

2009/0205085 A1    8/2009   Goldman et al.

FOREIGN PATENT DOCUMENTS

| JP | 2003-506024 A | 2/2003 | |
|----|---|---|---|
| WO | 01/09159 A1 | 2/2001 | |
| WO | WO 2010/131748 A1 * | 11/2010 | ........................ 514/44 |
| WO | WO 2011/007876 A1 * | 1/2011 | ........................ 514/44 |

OTHER PUBLICATIONS

Naomi Hirabayashi et al., Abstract of the 83rd Annual Meeting of the Japanese Biochemical Society and the 33rd Annual Meeting of the Molecular Biology Society of Japan, 2P-1258 (2010).
Naomi Hirabayashi et al., "Isolation of c-Met binding aptamer", Proceedings of 12th RNA Meeting in Tokyo), Jul. 27, 2010, pp. 236.
Ravi Salgia, "Role of c-Met in Cancer: Emphasis on Lung Cancer", Seminars in Oncology, Apr. 2009, pp. s52-s58, vol. 36, No. 2.
Shoutaro Tsuji et al., "RNA aptamer binding to polyhistidine-tag", Biochemical and Biophysical Research Communications, 2009, pp. 227-231, vol. 386.
Shoutaro Tsuji et al., "Effective isolation of RNA aptamer through suppression of PCR bias", Biochemical and Biophysical Communications, 2009, pp. 223-226, vol. 386.
International Search Report for PCT/JP2011/066962 dated Sep. 6, 2011.
Communication dated Jul. 4, 2014, issued by the European Patent Office in corresponding Application No. 11812479.1.

* cited by examiner

*Primary Examiner* — Amy Bowman
(74) *Attorney, Agent, or Firm* — Sughrue Mion, PLLC

(57) ABSTRACT

The present invention provides a nucleic acid molecule capable of binding to c-Met as a substance that can be used for clarification of the pathogenic mechanism of diseases caused by c-Met, diagnosis and treatment of the diseases, and the like, and also the use thereof. The c-Met binding nucleic acid molecule of the present invention is any one of the following nucleic acid molecules (A1), (A2), (B1), and (B2).

(A1) a nucleic acid molecule including the base sequence of any one of SEQ ID NOs: 1 to 38
(A2) a nucleic acid molecule that is capable of binding to c-Met and includes a base sequence obtained by substitution, deletion, addition, and/or insertion of one or more bases in the base sequence of any one of SEQ ID NOs: 1 to 38
(B1) a nucleic acid molecule including the base sequence of any one of SEQ ID NOs: 39 to 76
(B2) a nucleic acid molecule that is capable of binding to c-Met and includes a base sequence obtained by substitution, deletion, addition, and/or insertion of one or more bases in the base sequence of any one of SEQ ID NOs: 39 to 76.

12 Claims, 10 Drawing Sheets

```
SEQUENCE LISTING

<160> NUMBER OF SEQ ID NOS: 97

<210> SEQ ID NO 1
<211> LENGTH: 40
<212> TYPE: RNA
<213> ORGANISM: Artificial
<220> FEATURE:
<223> OTHER INFORMATION: aptamer

<400> SEQUENCE: 1
acacacugag aguuugacca gcuauuaaau gggucgugac                    40

<210> SEQ ID NO 2
<211> LENGTH: 40
<212> TYPE: RNA
<213> ORGANISM: Artificial
<220> FEATURE:
<223> OTHER INFORMATION: aptamer

<400> SEQUENCE: 2
acccuggcga ucuccggccg gauacgggag aacgagguac                    40

<210> SEQ ID NO 3
<211> LENGTH: 40
<212> TYPE: RNA
<213> ORGANISM: Artificial
<220> FEATURE:
<223> OTHER INFORMATION: aptamer

<400> SEQUENCE: 3
gggcgaaacu gucgugacac gguuugacau gccggccuua                    40

<210> SEQ ID NO 4
<211> LENGTH: 40
```

```
<212> TYPE: RNA
<213> ORGANISM: Artificial
<220> FEATURE:
<223> OTHER INFORMATION: aptamer

<400> SEQUENCE: 4
uaccgugauu cggggguggua uccgguggac auccaggucg                     40

<210> SEQ ID NO 5
<211> LENGTH: 40
<212> TYPE: RNA
<213> ORGANISM: Artificial
<220> FEATURE:
<223> OTHER INFORMATION: aptamer

<400> SEQUENCE: 5
gcccaacgaa cauuuugagu uuccaggcag cucauagaca                     40

<210> SEQ ID NO 6
<211> LENGTH: 40
<212> TYPE: RNA
<213> ORGANISM: Artificial
<220> FEATURE:
<223> OTHER INFORMATION: aptamer

<400> SEQUENCE: 6
uccaggugug gcgagccacu guaagagucg ccgugaggau                     40

<210> SEQ ID NO 7
<211> LENGTH: 40
<212> TYPE: RNA
<213> ORGANISM: Artificial
<220> FEATURE:
<223> OTHER INFORMATION: aptamer

<400> SEQUENCE: 7
cuugaaguca aggguagagu gaccaugcag cucguagaca                     40

<210> SEQ ID NO 8
<211> LENGTH: 40
<212> TYPE: RNA
<213> ORGANISM: Artificial
<220> FEATURE:
<223> OTHER INFORMATION: aptamer

<400> SEQUENCE: 8
gggcacuuaa aaccagaccg ugauuugcgg uuggucucgc                     40

<210> SEQ ID NO 9
<211> LENGTH: 40
<212> TYPE: RNA
<213> ORGANISM: Artificial
<220> FEATURE:
<223> OTHER INFORMATION: aptamer

<400> SEQUENCE: 9
gaugucucaa uuggucguga uugugcugac cacacgaacc                     40

<210> SEQ ID NO 10
<211> LENGTH: 40
<212> TYPE: RNA
<213> ORGANISM: Artificial
<220> FEATURE:
<223> OTHER INFORMATION: aptamer

<400> SEQUENCE: 10
```
acacagcucu gauggucgug auuagguuga ccaccuaccu          40

<210> SEQ ID NO 11
<211> LENGTH: 40
<212> TYPE: RNA
<213> ORGANISM: Artificial
<220> FEATURE:
<223> OTHER INFORMATION: aptamer

<400> SEQUENCE: 11
guuuaggugg caucgaccuu caugaaacgg gugcacaggc          40

<210> SEQ ID NO 12
<211> LENGTH: 40
<212> TYPE: RNA
<213> ORGANISM: Artificial
<220> FEATURE:
<223> OTHER INFORMATION: aptamer

<400> SEQUENCE: 12
cgcggccauc cggcguuugg aacgggaugu acaccugaca          40

<210> SEQ ID NO 13
<211> LENGTH: 40
<212> TYPE: RNA
<213> ORGANISM: Artificial
<220> FEATURE:
<223> OTHER INFORMATION: aptamer

<400> SEQUENCE: 13
ucacucggac agccggagcg aaacgggcug uguaagacug          40

<210> SEQ ID NO 14
<211> LENGTH: 40
<212> TYPE: RNA
<213> ORGANISM: Artificial
<220> FEATURE:
<223> OTHER INFORMATION: aptamer

<400> SEQUENCE: 14
ucaucgggac aucggaugga acggguguca agaagcgugu          40

<210> SEQ ID NO 15
<211> LENGTH: 40
<212> TYPE: RNA
<213> ORGANISM: Artificial
<220> FEATURE:
<223> OTHER INFORMATION: aptamer

<400> SEQUENCE: 15
gacgcgggcc accggcuagc gacggguggu aaagggcuug          40

<210> SEQ ID NO 16
<211> LENGTH: 40
<212> TYPE: RNA
<213> ORGANISM: Artificial
<220> FEATURE:
<223> OTHER INFORMATION: aptamer

<400> SEQUENCE: 16
ccgcuaccgg gugcaacggg uagacuguaa ccaggugaua          40

<210> SEQ ID NO 17
<211> LENGTH: 39
<212> TYPE: RNA
<213> ORGANISM: Artificial

```
<220> FEATURE:
<223> OTHER INFORMATION: aptamer

<400> SEQUENCE: 17
agugauggcc ggcuggagaa acgggccacu cgauccagg                              39

<210> SEQ ID NO 18
<211> LENGTH: 40
<212> TYPE: RNA
<213> ORGANISM: Artificial
<220> FEATURE:
<223> OTHER INFORMATION: aptamer

<400> SEQUENCE: 18
ggcacccuau aggauucagc cccuaacccg guguugugaa                             40

<210> SEQ ID NO 19
<211> LENGTH: 40
<212> TYPE: RNA
<213> ORGANISM: Artificial
<220> FEATURE:
<223> OTHER INFORMATION: aptamer

<400> SEQUENCE: 19
guagccguga uuggguuggc ugcccacaau uauccaggac                             40

<210> SEQ ID NO 20
<211> LENGTH: 39
<212> TYPE: RNA
<213> ORGANISM: Artificial
<220> FEATURE:
<223> OTHER INFORMATION: aptamer

<400> SEQUENCE: 20
acguuguggc gaacuucggc ccgaacggga guaacugca                              39

<210> SEQ ID NO 21
<211> LENGTH: 40
<212> TYPE: RNA
<213> ORGANISM: Artificial
<220> FEATURE:
<223> OTHER INFORMATION: aptamer

<400> SEQUENCE: 21
ccuugguguc auccgaccaa auuagaacgg gaugaggaag                             40

<210> SEQ ID NO 22
<211> LENGTH: 40
<212> TYPE: RNA
<213> ORGANISM: Artificial
<220> FEATURE:
<223> OTHER INFORMATION: aptamer

<400> SEQUENCE: 22
gcguguuucu ucauuucgac gcuggccaac ggaaaugcaa                             40

<210> SEQ ID NO 23
<211> LENGTH: 40
<212> TYPE: RNA
<213> ORGANISM: Artificial
<220> FEATURE:
<223> OTHER INFORMATION: aptamer

<400> SEQUENCE: 23
augggagugc gccucggcuc uaacggaggu augcacguca                             40
```

<210> SEQ ID NO 24
<211> LENGTH: 40
<212> TYPE: RNA
<213> ORGANISM: Artificial
<220> FEATURE:
<223> OTHER INFORMATION: aptamer

<400> SEQUENCE: 24
gaguugucgc acagcgacuc gaaaauaauc uguccgacac                              40

<210> SEQ ID NO 25
<211> LENGTH: 40
<212> TYPE: RNA
<213> ORGANISM: Artificial
<220> FEATURE:
<223> OTHER INFORMATION: aptamer

<400> SEQUENCE: 25
uagcaacagu ucccagaggu gaucaggcag ccuuaagaca                              40

<210> SEQ ID NO 26
<211> LENGTH: 39
<212> TYPE: RNA
<213> ORGANISM: Artificial
<220> FEATURE:
<223> OTHER INFORMATION: aptamer

<400> SEQUENCE: 26
gcuccaccag guguagcuag ccuguagaca ucaguagca                               39

<210> SEQ ID NO 27
<211> LENGTH: 40
<212> TYPE: RNA
<213> ORGANISM: Artificial
<220> FEATURE:
<223> OTHER INFORMATION: aptamer

<400> SEQUENCE: 27
ccuaugcaga ccgacauccg gguauacggg augaugcgac                              40

<210> SEQ ID NO 28
<211> LENGTH: 40
<212> TYPE: RNA
<213> ORGANISM: Artificial
<220> FEATURE:
<223> OTHER INFORMATION: aptamer

<400> SEQUENCE: 28 ccugggggu uccgcaggaau cgggaacuag auuggugguc                              40

<210> SEQ ID NO 29
<211> LENGTH: 40
<212> TYPE: RNA
<213> ORGANISM: Artificial
<220> FEATURE:
<223> OTHER INFORMATION: aptamer

<400> SEQUENCE: 29
acgagccgug auuggguugg caacccugcu uaugugagga                              40

<210> SEQ ID NO 30
<211> LENGTH: 40
<212> TYPE: RNA
<213> ORGANISM: Artificial
<220> FEATURE:
<223> OTHER INFORMATION: aptamer

```
<400> SEQUENCE: 30
aaauugccgg gaucuggugu ggcgaccaug cggcgugcau                              40

<210> SEQ ID NO 31
<211> LENGTH: 40
<212> TYPE: RNA
<213> ORGANISM: Artificial
<220> FEATURE:
<223> OTHER INFORMATION: aptamer

<400> SEQUENCE: 31
agagucuaug ccgugaguga ggguggcgcc ucgacugcca                              40

<210> SEQ ID NO 32
<211> LENGTH: 40
<212> TYPE: RNA
<213> ORGANISM: Artificial
<220> FEATURE:
<223> OTHER INFORMATION: aptamer

<400> SEQUENCE: 32
acaagaccgg gauggggguu ggucacacac aaagacugaa                              40

<210> SEQ ID NO 33
<211> LENGTH: 40
<212> TYPE: RNA
<213> ORGANISM: Artificial
<220> FEATURE:
<223> OTHER INFORMATION: aptamer

<400> SEQUENCE: 33
acuuuuggcg aucuccggcc ggauacggga gaacgaggua                              40

<210> SEQ ID NO 34
<211> LENGTH: 40
<212> TYPE: RNA
<213> ORGANISM: Artificial
<220> FEATURE:
<223> OTHER INFORMATION: aptamer

<400> SEQUENCE: 34
uuuggugaau uccgaccauu uugcaaacgg gauacgggac                              40

<210> SEQ ID NO 35
<211> LENGTH: 40
<212> TYPE: RNA
<213> ORGANISM: Artificial
<220> FEATURE:
<223> OTHER INFORMATION: aptamer

<400> SEQUENCE: 35
gauuugugug auacccgaca cucuaacggg guagcagggc                              40

<210> SEQ ID NO 36
<211> LENGTH: 40
<212> TYPE: RNA
<213> ORGANISM: Artificial
<220> FEATURE:
<223> OTHER INFORMATION: aptamer

<400> SEQUENCE: 36
cuugauuggu cgcaaccgga caaggacggg uugaugcagu                              40

<210> SEQ ID NO 37
```

```
<211> LENGTH: 40
<212> TYPE: RNA
<213> ORGANISM: Artificial
<220> FEATURE:
<223> OTHER INFORMATION: aptamer

<400> SEQUENCE: 37
gguuugcucc gaccgacuaa agggagccuc ugucacgagu                    40

<210> SEQ ID NO 38
<211> LENGTH: 40
<212> TYPE: RNA
<213> ORGANISM: Artificial
<220> FEATURE:
<223> OTHER INFORMATION: aptamer

<400> SEQUENCE: 38
ccaggagcau uagaccgggg aaagaaggag uaccgucugg                    40

<210> SEQ ID NO 39
<211> LENGTH: 80
<212> TYPE: RNA
<213> ORGANISM: Artificial
<220> FEATURE:
<223> OTHER INFORMATION: aptamer

<400> SEQUENCE: 39
gggacgcuca cguacgcuaa acacacugag aguuugacca gcuauuaaau gggucgugac    60
ucagugccug gacgugcagu                                              80

<210> SEQ ID NO 40
<211> LENGTH: 80
<212> TYPE: RNA
<213> ORGANISM: Artificial
<220> FEATURE:
<223> OTHER INFORMATION: aptamer

<400> SEQUENCE: 40
gggacgcuca cguacgcuaa acccuggcga ucuccggccg gauacgggag aacgagguac    60
ucagugccug gacgugcagu                                              80

<210> SEQ ID NO 41
<211> LENGTH: 80
<212> TYPE: RNA
<213> ORGANISM: Artificial
<220> FEATURE:
<223> OTHER INFORMATION: aptamer

<400> SEQUENCE: 41
gggacgcuca cguacgcuaa gggcgaaacu gucgugacac gguuugacau gccggccuua    60
ucagugccug gacgugcagu                                              80

<210> SEQ ID NO 42
<211> LENGTH: 80
<212> TYPE: RNA
<213> ORGANISM: Artificial
<220> FEATURE:
<223> OTHER INFORMATION: aptamer

<400> SEQUENCE: 42
gggacgcuca cguacgcuaa uaccgugauu cggggugggua uccgguggac auccaggucg    60
ucagugccug gacgugcagu                                              80
```

```
<210> SEQ ID NO 43
<211> LENGTH: 80
<212> TYPE: RNA
<213> ORGANISM: Artificial
<220> FEATURE:
<223> OTHER INFORMATION: aptamer

<400> SEQUENCE: 43
gggacgcuca cguacgcuaa gcccaacgaa cauuuugagu uccaggcag cucauagaca     60 ucagugccug gacgugcagu                                               80

<210> SEQ ID NO 44
<211> LENGTH: 80
<212> TYPE: RNA
<213> ORGANISM: Artificial
<220> FEATURE:
<223> OTHER INFORMATION: aptamer

<400> SEQUENCE: 44
gggacgcuca cguacgcuaa uccaggugug gcgagccacu guaagagucg ccgugaggau    60
ucagugccug gacgugcagu                                               80

<210> SEQ ID NO 45
<211> LENGTH: 80
<212> TYPE: RNA
<213> ORGANISM: Artificial
<220> FEATURE:
<223> OTHER INFORMATION: aptamer

<400> SEQUENCE: 45
gggacgcuca cguacgcuaa cuugaaguca aggguagagu gaccaugcag cucguagaca    60
ucagugccug gacgugcagu                                               80

<210> SEQ ID NO 46
<211> LENGTH: 80
<212> TYPE: RNA
<213> ORGANISM: Artificial
<220> FEATURE:
<223> OTHER INFORMATION: aptamer

<400> SEQUENCE: 46
gggacgcuca cguacgcuaa gggcacuuaa aaccagaccg ugauuugcgg uuggucucgc    60
ucagugccug gacgugcagu                                               80

<210> SEQ ID NO 47
<211> LENGTH: 80
<212> TYPE: RNA
<213> ORGANISM: Artificial
<220> FEATURE:
<223> OTHER INFORMATION: aptamer

<400> SEQUENCE: 47
gggacgcuca cguacgcuaa gaugucucaa uuggucguga uugugcugac cacacgaacc    60
ucagugccug gacgugcagu                                               80

<210> SEQ ID NO 48
<211> LENGTH: 80
<212> TYPE: RNA
<213> ORGANISM: Artificial
<220> FEATURE:
<223> OTHER INFORMATION: aptamer

<400> SEQUENCE: 48
```

```
gggacgcuca cguacgcuaa acacagcucu gauggucgug auuagguuga ccaccuaccu    60
ucagugccug gacgugcagu                                                80

<210> SEQ ID NO 49
<211> LENGTH: 80
<212> TYPE: RNA
<213> ORGANISM: Artificial
<220> FEATURE:
<223> OTHER INFORMATION: aptamer

<400> SEQUENCE: 49
gggacgcuca cguacgcuaa guuuaggugg caucgaccuu caugaaacgg gugcacaggc    60
ucagugccug gacgugcagu                                                80

<210> SEQ ID NO 50
<211> LENGTH: 80
<212> TYPE: RNA
<213> ORGANISM: Artificial
<220> FEATURE:
<223> OTHER INFORMATION: aptamer

<400> SEQUENCE: 50
gggacgcuca cguacgcuaa cgcggccauc cggcguuugg aacgggaugu acaccugaca    60
ucagugccug gacgugcagu                                                80

<210> SEQ ID NO 51
<211> LENGTH: 80
<212> TYPE: RNA
<213> ORGANISM: Artificial
<220> FEATURE:
<223> OTHER INFORMATION: aptamer

<400> SEQUENCE: 51
gggacgcuca cguacgcuaa ucacucggac agccggagcg aaacgggcug uguaagacug    60
ucagugccug gacgugcagu                                                80

<210> SEQ ID NO 52
<211> LENGTH: 80
<212> TYPE: RNA
<213> ORGANISM: Artificial
<220> FEATURE:
<223> OTHER INFORMATION: aptamer

<400> SEQUENCE: 52
gggacgcuca cguacgcuaa ucaucgggac aucggaugga acggguguca agaagcgugu    60
ucagugccug gacgugcagu                                                80

<210> SEQ ID NO 53
<211> LENGTH: 80
<212> TYPE: RNA
<213> ORGANISM: Artificial
<220> FEATURE:
<223> OTHER INFORMATION: aptamer

<400> SEQUENCE: 53
gggacgcuca cguacgcuaa gacgcgggcc accggcuagc gacggugguu aaagggcuug    60
ucagugccug gacgugcagu                                                80

<210> SEQ ID NO 54
<211> LENGTH: 80
<212> TYPE: RNA
<213> ORGANISM: Artificial
```

```
<220> FEATURE:
<223> OTHER INFORMATION: aptamer

<400> SEQUENCE: 54
gggacgcuca cguacgcuaa ccgcuaccgg gugcaacggg uagacuguaa ccaggugaua    60
ucagugccug gacgugcagu                                                80

<210> SEQ ID NO 55
<211> LENGTH: 79
<212> TYPE: RNA
<213> ORGANISM: Artificial
<220> FEATURE:
<223> OTHER INFORMATION: aptamer

<400> SEQUENCE: 55
gggacgcuca cguacgcuaa agugauggcc ggcuggagaa acgggccacu cgauccaggu    60
cagugccugg acgugcagu                                                 79

<210> SEQ ID NO 56
<211> LENGTH: 80
<212> TYPE: RNA
<213> ORGANISM: Artificial
<220> FEATURE:
<223> OTHER INFORMATION: aptamer

<400> SEQUENCE: 56
gggacgcuca cguacgcuaa ggcacccuau aggauucagc cccuaacccg guguugugaa    60
ucagugccug gacgugcagu                                                80

<210> SEQ ID NO 57
<211> LENGTH: 80
<212> TYPE: RNA
<213> ORGANISM: Artificial
<220> FEATURE:
<223> OTHER INFORMATION: aptamer

<400> SEQUENCE: 57
gggacgcuca cguacgcuaa guagccguga uuggguuggc ugcccacaau uauccaggac    60
ucagugccug gacgugcagu                                                80

<210> SEQ ID NO 58
<211> LENGTH: 79
<212> TYPE: RNA
<213> ORGANISM: Artificial
<220> FEATURE:
<223> OTHER INFORMATION: aptamer

<400> SEQUENCE: 58
gggacgcuca cguacgcuaa acguugggc gaacuucggc ccgaacggga guaacugcau     60
cagugccugg acgugcagu                                                 79

<210> SEQ ID NO 59
<211> LENGTH: 80
<212> TYPE: RNA
<213> ORGANISM: Artificial
<220> FEATURE:
<223> OTHER INFORMATION: aptamer

<400> SEQUENCE: 59
gggacgcuca cguacgcuaa ccuuggeguc auccgaccaa auuagaacgg gaugaggaag    60
ucagugccug gacgugcagu                                                80
```

```
<210> SEQ ID NO 60
<211> LENGTH: 80
<212> TYPE: RNA
<213> ORGANISM: Artificial
<220> FEATURE:
<223> OTHER INFORMATION: aptamer

<400> SEQUENCE: 60
gggacgcuca cguacgcuaa gcguguuucu ucauuucgac gcuggccaac ggaaaugcaa    60
ucagugccug gacgugcagu                                               80

<210> SEQ ID NO 61
<211> LENGTH: 80
<212> TYPE: RNA
<213> ORGANISM: Artificial
<220> FEATURE:
<223> OTHER INFORMATION: aptamer

<400> SEQUENCE: 61
gggacgcuca cguacgcuaa augggagugc gccucggcuc uaacggaggu augcacguca    60
ucagugccug gacgugcagu                                               80

<210> SEQ ID NO 62
<211> LENGTH: 80
<212> TYPE: RNA
<213> ORGANISM: Artificial
<220> FEATURE:
<223> OTHER INFORMATION: aptamer

<400> SEQUENCE: 62
gggacgcuca cguacgcuaa gaguugucgc acagcgacuc gaaaauaauc uguccgacac    60
ucagugccug gacgugcagu                                               80

<210> SEQ ID NO 63
<211> LENGTH: 80
<212> TYPE: RNA
<213> ORGANISM: Artificial
<220> FEATURE:
<223> OTHER INFORMATION: aptamer

<400> SEQUENCE: 63
gggacgcuca cguacgcuaa uagcaacagu ucccagaggu gaucaggcag ccuuaagaca    60
ucagugccug gacgugcagu                                               80

<210> SEQ ID NO 64
<211> LENGTH: 79
<212> TYPE: RNA
<213> ORGANISM: Artificial
<220> FEATURE:
<223> OTHER INFORMATION: aptamer

<400> SEQUENCE: 64
gggacgcuca cguacgcuaa gcuccaccag guguagcuag ccuguagaca ucaguagcau    60
cagugccugg acgugcagu                                                79

<210> SEQ ID NO 65
<211> LENGTH: 80
<212> TYPE: RNA
<213> ORGANISM: Artificial
<220> FEATURE:
<223> OTHER INFORMATION: aptamer

<400> SEQUENCE: 65
```

-continued gggacgcuca cguacgcuaa ccuaugcaga ccgacauccg gguauacggg augaugcgac    60
ucagugccug gacgugcagu                                               80

<210> SEQ ID NO 66
<211> LENGTH: 80
<212> TYPE: RNA
<213> ORGANISM: Artificial
<220> FEATURE:
<223> OTHER INFORMATION: aptamer

<400> SEQUENCE: 66
gggacgcuca cguacgcuaa ccuggggguu ccgcaggaau cgggaacuag auugguggguc   60 ucagugccug gacgugcagu                                               80

<210> SEQ ID NO 67
<211> LENGTH: 80
<212> TYPE: RNA
<213> ORGANISM: Artificial
<220> FEATURE:
<223> OTHER INFORMATION: aptamer

<400> SEQUENCE: 67
gggacgcuca cguacgcuaa acgagccgug auugggnugg caaccugcu uaugugagga    60 ucagugccug gacgugcagu                                               80

<210> SEQ ID NO 68
<211> LENGTH: 80
<212> TYPE: RNA
<213> ORGANISM: Artificial
<220> FEATURE:
<223> OTHER INFORMATION: aptamer

<400> SEQUENCE: 68
gggacgcuca cguacgcuaa aaauugccgg gaucuggugu ggcgaccaug cggcgugcau    60
ucagugccug gacgugcagu                                               80

<210> SEQ ID NO 69
<211> LENGTH: 80
<212> TYPE: RNA
<213> ORGANISM: Artificial
<220> FEATURE:
<223> OTHER INFORMATION: aptamer

<400> SEQUENCE: 69
gggacgcuca cguacgcuaa agagucuaug ccgugaguga ggguggcgcc ucgacugcca    60
ucagugccug gacgugcagu                                               80

<210> SEQ ID NO 70
<211> LENGTH: 80
<212> TYPE: RNA
<213> ORGANISM: Artificial
<220> FEATURE:
<223> OTHER INFORMATION: aptamer

<400> SEQUENCE: 70
gggacgcuca cguacgcuaa acaagaccgg gauggggguu ggucacacac aaagacugaa    60
ucagugccug gacgugcagu                                               80

<210> SEQ ID NO 71
<211> LENGTH: 80
<212> TYPE: RNA

```
<213> ORGANISM: Artificial
<220> FEATURE:
<223> OTHER INFORMATION: aptamer

<400> SEQUENCE: 71
gggacgcuca cguacgcuaa acuuuuggcg aucuccggcc ggauacggga gaacgaggua      60
ucagugccug gacgugcagu                                                  80

<210> SEQ ID NO 72
<211> LENGTH: 80
<212> TYPE: RNA
<213> ORGANISM: Artificial
<220> FEATURE:
<223> OTHER INFORMATION: aptamer

<400> SEQUENCE: 72
gggacgcuca cguacgcuaa uuuggugaau uccgaccauu uugcaaacgg gauacgggac      60
ucagugccug gacgugcagu                                                  80

<210> SEQ ID NO 73
<211> LENGTH: 80
<212> TYPE: RNA
<213> ORGANISM: Artificial
<220> FEATURE:
<223> OTHER INFORMATION: aptamer

<400> SEQUENCE: 73
gggacgcuca cguacgcuaa gauuugugug auacccgaca cucuaacggg guagcagggc      60
ucagugccug gacgugcagu                                                  80

<210> SEQ ID NO 74
<211> LENGTH: 80
<212> TYPE: RNA
<213> ORGANISM: Artificial
<220> FEATURE:
<223> OTHER INFORMATION: aptamer

<400> SEQUENCE: 74
gggacgcuca cguacgcuaa cuugauuggu cgcaaccgga caaggacggg uugaugcagu      60
ucagugccug gacgugcagu                                                  80

<210> SEQ ID NO 75
<211> LENGTH: 80
<212> TYPE: RNA
<213> ORGANISM: Artificial
<220> FEATURE:
<223> OTHER INFORMATION: aptamer

<400> SEQUENCE: 75
gggacgcuca cguacgcuaa gguuugcucc gaccgacuaa agggagccuc ugucacgagu      60
ucagugccug gacgugcagu                                                  80

<210> SEQ ID NO 76
<211> LENGTH: 80
<212> TYPE: RNA
<213> ORGANISM: Artificial
<220> FEATURE:
<223> OTHER INFORMATION: aptamer

<400> SEQUENCE: 76
gggacgcuca cguacgcuaa ccaggagcau uagaccgggg aaagaaggag uaccgucugg      60
ucagugccug gacgugcagu                                                  80
```

```
<210> SEQ ID NO 77
<211> LENGTH: 20
<212> TYPE: RNA
<213> ORGANISM: Artificial
<220> FEATURE:
<223> OTHER INFORMATION: aptamer

<400> SEQUENCE: 77
gggacgcuca cguacgcuaa                                              20

<210> SEQ ID NO 78
<211> LENGTH: 17
<212> TYPE: RNA
<213> ORGANISM: Artificial
<220> FEATURE:
<223> OTHER INFORMATION: aptamer

<400> SEQUENCE: 78
acgcucacgu acgcuaa                                                 17

<210> SEQ ID NO 79
<211> LENGTH: 20
<212> TYPE: RNA
<213> ORGANISM: Artificial
<220> FEATURE:
<223> OTHER INFORMATION: aptamer

<400> SEQUENCE: 79
ucagugccug gacgugcagu                                              20

<210> SEQ ID NO 80
<211> LENGTH: 1391
<212> TYPE: PRT
<213> ORGANISM: Artificial
<220> FEATURE:
<223> OTHER INFORMATION: recombinant c-Met
<220> FEATURE:
<221> NAME/KEY: misc_feature
<222> LOCATION: (1381)..(1381)
<223> OTHER INFORMATION: Xaa stands for any amino acid

<400> SEQUENCE: 80
```

Met Lys Ala Pro Ala Val Leu Ala Pro Gly Ile Leu Val Leu Leu Phe
 1               5                  10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys

-continued

```
            145                 150                 155                 160
        Ile Phe Ser Pro Gln Ile Glu Glu Pro Ser Gln Cys Pro Asp Cys Val
                        165                 170                 175
        Val Ser Ala Leu Gly Ala Lys Val Leu Ser Ser Val Lys Asp Arg Phe
                        180                 185                 190
        Ile Asn Phe Phe Val Gly Asn Thr Ile Asn Ser Ser Tyr Phe Pro Asp
                        195                 200                 205
        His Pro Leu His Ser Ile Ser Val Arg Arg Leu Lys Glu Thr Lys Asp
            210                 215                 220
        Gly Phe Met Phe Leu Thr Asp Gln Ser Tyr Ile Asp Val Leu Pro Glu
        225                 230                 235                 240
        Phe Arg Asp Ser Tyr Pro Ile Lys Tyr Val His Ala Phe Glu Ser Asn
                        245                 250                 255
        Asn Phe Ile Tyr Phe Leu Thr Val Gln Arg Glu Thr Leu Asp Ala Gln
                        260                 265                 270
        Thr Phe His Thr Arg Ile Ile Arg Phe Cys Ser Ile Asn Ser Gly Leu
                        275                 280                 285
        His Ser Tyr Met Glu Met Pro Leu Glu Cys Ile Leu Thr Glu Lys Arg
            290                 295                 300
        Lys Lys Arg Ser Thr Lys Lys Glu Val Phe Asn Ile Leu Gln Ala Ala
        305                 310                 315                 320
        Tyr Val Ser Lys Pro Gly Ala Gln Leu Ala Arg Gln Ile Gly Ala Ser
                        325                 330                 335
        Leu Asn Asp Asp Ile Leu Phe Gly Val Phe Ala Gln Ser Lys Pro Asp
                        340                 345                 350
        Ser Ala Glu Pro Met Asp Arg Ser Ala Met Cys Ala Phe Pro Ile Lys
                        355                 360                 365
        Tyr Val Asn Asp Phe Phe Asn Lys Ile Val Asn Lys Asn Asn Val Arg
                        370                 375                 380
        Cys Leu Gln His Phe Tyr Gly Pro Asn His Glu His Cys Phe Asn Arg
        385                 390                 395                 400
        Thr Leu Leu Arg Asn Ser Ser Gly Cys Glu Ala Arg Arg Asp Glu Tyr
                        405                 410                 415
        Arg Thr Glu Phe Thr Thr Ala Leu Gln Arg Val Asp Leu Phe Met Gly
                        420                 425                 430
        Gln Phe Ser Glu Val Leu Leu Thr Ser Ile Ser Thr Phe Ile Lys Gly
                        435                 440                 445
        Asp Leu Thr Ile Ala Asn Leu Gly Thr Ser Glu Gly Arg Phe Met Gln
            450                 455                 460
        Val Val Val Ser Arg Ser Gly Pro Ser Thr Pro His Val Asn Phe Leu
        465                 470                 475                 480
        Leu Asp Ser His Pro Val Ser Pro Glu Val Ile Val Glu His Thr Leu
                        485                 490                 495
        Asn Gln Asn Gly Tyr Thr Leu Val Ile Thr Gly Lys Lys Ile Thr Lys
                        500                 505                 510
        Ile Pro Leu Asn Gly Leu Gly Cys Arg His Phe Gln Ser Cys Ser Gln
                        515                 520                 525
        Cys Leu Ser Ala Pro Pro Phe Val Gln Cys Gly Trp Cys His Asp Lys
                        530                 535                 540
        Cys Val Arg Ser Glu Glu Cys Leu Ser Gly Thr Trp Thr Gln Gln Ile
        545                 550                 555                 560
        Cys Leu Pro Ala Ile Tyr Lys Val Phe Pro Asn Ser Ala Pro Leu Glu
                        565                 570                 575
```

```
Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990
```

```
Thr Glu Met Val Ser Asn Glu Ser  Val Asp Tyr Arg Ala  Thr Phe Pro
            995                 1000                 1005

Glu Asp Gln Phe Pro Asn Ser  Ser Gln Asn Gly Ser  Cys Arg Gln
    1010                1015                 1020

Val Gln Tyr Pro Leu Thr Asp  Met Ser Pro Ile Leu  Thr Ser Gly
    1025                1030                 1035

Asp Ser Asp Ile Ser Ser Pro  Leu Leu Gln Asn Thr  Val His Ile
    1040                1045                 1050

Asp Leu Ser Ala Leu Asn Pro  Glu Leu Val Gln Ala  Val Gln His
    1055                1060                 1065

Val Val Ile Gly Pro Ser Ser  Leu Ile Val His Phe  Asn Glu Val
    1070                1075                 1080

Ile Gly Arg Gly His Phe Gly  Cys Val Tyr His Gly  Thr Leu Leu
    1085                1090                 1095

Asp Asn Asp Gly Lys Lys Ile  His Cys Ala Val Lys  Ser Leu Asn
    1100                1105                 1110

Arg Ile Thr Asp Ile Gly Glu  Val Ser Gln Phe Leu  Thr Glu Gly
    1115                1120                 1125

Ile Ile Met Lys Asp Phe Ser  His Pro Asn Val Leu  Ser Leu Leu
    1130                1135                 1140

Gly Ile Cys Leu Arg Ser Glu  Gly Ser Pro Leu Val  Val Leu Pro
    1145                1150                 1155

Tyr Met Lys His Gly Asp Leu  Arg Asn Phe Ile Arg  Asn Glu Thr
    1160                1165                 1170

His Asn Pro Thr Val Lys Asp  Leu Ile Gly Phe Gly  Leu Gln Val
    1175                1180                 1185

Ala Lys Gly Met Lys Tyr Leu  Ala Ser Lys Lys Phe  Val His Arg
    1190                1195                 1200

Asp Leu Ala Ala Arg Asn Cys  Met Leu Asp Glu Lys  Phe Thr Val
    1205                1210                 1215

Lys Val Ala Asp Phe Gly Leu  Ala Arg Asp Met Tyr  Asp Lys Glu
    1220                1225                 1230

Tyr Tyr Ser Val His Asn Lys  Thr Gly Ala Lys Leu  Pro Val Lys
    1235                1240                 1245

Trp Met Ala Leu Glu Ser Leu  Gln Thr Gln Lys Phe  Thr Thr Lys
    1250                1255                 1260

Ser Asp Val Trp Ser Phe Gly  Val Leu Leu Trp Glu  Leu Met Thr
    1265                1270                 1275

Arg Gly Ala Pro Pro Tyr Pro  Asp Val Asn Thr Phe  Asp Ile Thr
    1280                1285                 1290

Val Tyr Leu Leu Gln Gly Arg  Arg Leu Leu Gln Pro  Glu Tyr Cys
    1295                1300                 1305

Pro Asp Pro Leu Tyr Glu Val  Met Leu Lys Cys Trp  His Pro Lys
    1310                1315                 1320

Ala Glu Met Arg Pro Ser Phe  Ser Glu Leu Val Ser  Arg Ile Ser
    1325                1330                 1335

Ala Ile Phe Ser Thr Phe Ile  Gly Glu His Tyr Val  His Val Asn
    1340                1345                 1350

Ala Thr Tyr Val Asn Val Lys  Cys Val Ala Pro Tyr  Pro Ser Leu
    1355                1360                 1365

Leu Ser Ser Glu Asp Asn Ala  Asp Asp Glu Val Asp  Xaa Thr Arg
    1370                1375                 1380

Pro Ala Ser Phe Trp Glu Thr  Ser
```

-continued

```
                  1385              1390

<210> SEQ ID NO 81
<211> LENGTH: 74
<212> TYPE: RNA
<213> ORGANISM: Artificial
<220> FEATURE:
<223> OTHER INFORMATION: aptamer

<400> SEQUENCE: 81
gggcacguac gcuaaacaca cugagaguuu gaccagcuau uaaaugdgguc gugacucagu    60 gccuggacgu gcag                                                      74

<210> SEQ ID NO 82
<211> LENGTH: 67
<212> TYPE: RNA
<213> ORGANISM: Artificial
<220> FEATURE:
<223> OTHER INFORMATION: aptamer

<400> SEQUENCE: 82
gggacgcuaa acacacugag aguuugacca gcuauuaaau ggucgugac ucagugccug     60 gacgugc                                                              67

<210> SEQ ID NO 83
<211> LENGTH: 56
<212> TYPE: RNA
<213> ORGANISM: Artificial
<220> FEATURE:
<223> OTHER INFORMATION: aptamer

<400> SEQUENCE: 83
gggcacugag aguuugacca gcuauuaaau ggucgugac ucagugccug gacgug         56

<210> SEQ ID NO 84
<211> LENGTH: 75
<212> TYPE: RNA
<213> ORGANISM: Artificial
<220> FEATURE:
<223> OTHER INFORMATION: aptamer

<400> SEQUENCE: 84
gggacgcuca cguacgcuaa acacacugag aguuugacca gcuauuaaau gggucgugac    60
ucagugccug gacgu                                                     75

<210> SEQ ID NO 85
<211> LENGTH: 70
<212> TYPE: RNA
<213> ORGANISM: Artificial
<220> FEATURE:
<223> OTHER INFORMATION: aptamer

<400> SEQUENCE: 85
gggacgcuca cguacgcuaa acacacugag aguuugacca gcuauuaaau gggucgugac    60
ucagugccug                                                           70

<210> SEQ ID NO 86
<211> LENGTH: 46
<212> TYPE: RNA
<213> ORGANISM: Artificial
<220> FEATURE:
<223> OTHER INFORMATION: aptamer

<400> SEQUENCE: 86
```

```
gggcacugag aguuugacca gcuauuaaau gggucgugac ucagug        46
```

<210> SEQ ID NO 87
<211> LENGTH: 44
<212> TYPE: RNA
<213> ORGANISM: Artificial
<220> FEATURE:
<223> OTHER INFORMATION: aptamer

<400> SEQUENCE: 87

```
gggacugaga guuugaccag cuauuaaaug ggucgugacu cagu          44
```

<210> SEQ ID NO 88
<211> LENGTH: 42
<212> TYPE: RNA
<213> ORGANISM: Artificial
<220> FEATURE:
<223> OTHER INFORMATION: aptamer

<400> SEQUENCE: 88

```
gggcugagag uuugaccagc uauuaaaugg gucgugacuc ag            42
```

<210> SEQ ID NO 89
<211> LENGTH: 40
<212> TYPE: RNA
<213> ORGANISM: Artificial
<220> FEATURE:
<223> OTHER INFORMATION: aptamer

<400> SEQUENCE: 89

```
gggugagagu uugaccagcu auuaaauggg ucgugacuca              40
```

<210> SEQ ID NO 90
<211> LENGTH: 80
<212> TYPE: RNA
<213> ORGANISM: Artificial
<220> FEATURE:
<223> OTHER INFORMATION: aptamer
<220> FEATURE:
<221> NAME/KEY: misc_feature
<222> LOCATION: (21)..(60)
<223> OTHER INFORMATION: n stands for any base

<400> SEQUENCE: 90

```
gggacgcuca cguacgcuca nnnnnnnnnn nnnnnnnnnn nnnnnnnnnn nnnnnnnnnn    60
ucagugccug gacgugcagu                                               80
```

<210> SEQ ID NO 91
<211> LENGTH: 283
<212> TYPE: PRT
<213> ORGANISM: Homo sapiens

<400> SEQUENCE: 91

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Gln Leu Ile Ser Cys Gly Ser Val
            100                 105                 110

Asn Arg Gly Thr Cys Gln Arg His Val Phe Pro His Asn His Thr Ala
            115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
            195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg
            275                 280

<210> SEQ ID NO 92
<211> LENGTH: 625
<212> TYPE: PRT
<213> ORGANISM: Homo sapiens

<400> SEQUENCE: 92

Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
            20                  25                  30

Asp Ile Leu Phe Gly Val Phe Ala Gln Ser Lys Pro Asp Ser Ala Glu
        35                  40                  45

Pro Met Asp Arg Ser Ala Met Cys Ala Phe Pro Ile Lys Tyr Val Asn
    50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Thr Glu
            100                 105                 110

Phe Thr Thr Ala Leu Gln Arg Val Asp Leu Phe Met Gly Gln Phe Ser
        115                 120                 125

Glu Val Leu Leu Thr Ser Ile Ser Thr Phe Ile Lys Gly Asp Leu Thr
    130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser

```
                165                 170                 175
His Pro Val Ser Pro Glu Val Ile Val Glu His Thr Leu Asn Gln Asn
            180                 185                 190
Gly Tyr Thr Leu Val Ile Thr Gly Lys Lys Ile Thr Lys Ile Pro Leu
            195                 200                 205
Asn Gly Leu Gly Cys Arg His Phe Gln Ser Cys Ser Gln Cys Leu Ser
            210                 215                 220
Ala Pro Pro Phe Val Gln Cys Gly Trp Cys His Asp Lys Cys Val Arg
225                 230                 235                 240
Ser Glu Glu Cys Leu Ser Gly Thr Trp Thr Gln Gln Ile Cys Leu Pro
                245                 250                 255
Ala Ile Tyr Lys Val Phe Pro Asn Ser Ala Pro Leu Glu Gly Gly Thr
                260                 265                 270
Arg Leu Thr Ile Cys Gly Trp Asp Phe Gly Phe Arg Arg Asn Asn Lys
                275                 280                 285
Phe Asp Leu Lys Lys Thr Arg Val Leu Leu Gly Asn Glu Ser Cys Thr
            290                 295                 300
Leu Thr Leu Ser Glu Ser Thr Met Asn Thr Leu Lys Cys Thr Val Gly
305                 310                 315                 320
Pro Ala Met Asn Lys His Phe Asn Met Ser Ile Ile Ser Asn Gly
                325                 330                 335
His Gly Thr Thr Gln Tyr Ser Thr Phe Ser Tyr Val Asp Pro Val Ile
                340                 345                 350
Thr Ser Ile Ser Pro Lys Tyr Gly Pro Met Ala Gly Gly Thr Leu Leu
                355                 360                 365
Thr Leu Thr Gly Asn Tyr Leu Asn Ser Gly Asn Ser Arg His Ile Ser
            370                 375                 380
Ile Gly Gly Lys Thr Cys Thr Leu Lys Ser Val Ser Asn Ser Ile Leu
385                 390                 395                 400
Glu Cys Tyr Thr Pro Ala Gln Thr Ile Ser Thr Glu Phe Ala Val Lys
                405                 410                 415
Leu Lys Ile Asp Leu Ala Asn Arg Glu Thr Ser Ile Phe Ser Tyr Arg
            420                 425                 430
Glu Asp Pro Ile Val Tyr Glu Ile His Pro Thr Lys Ser Phe Ile Ser
            435                 440                 445
Gly Gly Ser Thr Ile Thr Gly Val Gly Lys Asn Leu Asn Ser Val Ser
            450                 455                 460
Val Pro Arg Met Val Ile Asn Val His Glu Ala Gly Arg Asn Phe Thr
465                 470                 475                 480
Val Ala Cys Gln His Arg Ser Asn Ser Glu Ile Ile Cys Cys Thr Thr
                485                 490                 495
Pro Ser Leu Gln Gln Leu Asn Leu Gln Leu Pro Leu Lys Thr Lys Ala
                500                 505                 510
Phe Phe Met Leu Asp Gly Ile Leu Ser Lys Tyr Phe Asp Leu Ile Tyr
                515                 520                 525
Val His Asn Pro Val Phe Lys Pro Phe Glu Lys Pro Val Met Ile Ser
            530                 535                 540
Met Gly Asn Glu Asn Val Leu Glu Ile Lys Gly Asn Asp Ile Asp Pro
545                 550                 555                 560
Glu Ala Val Lys Gly Glu Val Leu Lys Val Gly Asn Lys Ser Cys Glu
                565                 570                 575
Asn Ile His Leu His Ser Glu Ala Val Leu Cys Thr Val Pro Asn Asp
            580                 585                 590
```

-continued

```
Leu Leu Lys Leu Asn Ser Glu Leu Asn Ile Glu Trp Lys Gln Ala Ile
        595                 600                 605

Ser Ser Thr Val Leu Gly Lys Val Ile Val Gln Pro Asp Gln Asn Phe
610                 615                 620

Thr
625

<210> SEQ ID NO 93
<211> LENGTH: 7
<212> TYPE: PRT
<213> ORGANISM: Artificial
<220> FEATURE:
<223> OTHER INFORMATION: tag peptide

<400> SEQUENCE: 93

His Ile Glu Gly Arg Met Asp
1               5

<210> SEQ ID NO 94
<211> LENGTH: 231
<212> TYPE: PRT
<213> ORGANISM: Homo sapiens

<400> SEQUENCE: 94

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 95
<211> LENGTH: 6
```

```
<212> TYPE: PRT
<213> ORGANISM: Artificial
<220> FEATURE:
<223> OTHER INFORMATION: tag peptide

<400> SEQUENCE: 95

His His His His His His
1               5

<210> SEQ ID NO 96
<211> LENGTH: 222
<212> TYPE: PRT
<213> ORGANISM: Homo sapiens

<400> SEQUENCE: 96

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn
    210                 215                 220

<210> SEQ ID NO 97
<211> LENGTH: 7
<212> TYPE: PRT
<213> ORGANISM: Artificial
<220> FEATURE:
<223> OTHER INFORMATION: tag peptide

<400> SEQUENCE: 97

Asp Ile Glu Gly Arg Met Asp
1               5
```

NUCLEIC ACID MOLECULE CAPABLE OF BINDING TO C-MET AND USE THEREOF

CROSS REFERENCE TO RELATED APPLICATIONS

This application is a National Stage of International Application No. PCT/JP2011/066962 filed Jul. 26, 2011, claiming priority based on Japanese Patent Application No. 2010-167342 filed Jul. 26, 2010, the contents of all of which are incorporated herein by reference in their entirety.

TECHNICAL FIELD

The present invention relates to a nucleic acid molecule that binds to a c-Met protein and the use thereof.

BACKGROUND ART

The c-Met protein (hepatocyte growth factor receptor: HGFR, hereinafter referred to as "c-Met") is a receptor tyrosine kinase and is known as a receptor for a hepatocyte growth factor (HGF). c-Met is a heterodimer membrane protein composed of an α chain and a β chain, and the β chain is composed of a tyrosine kinase domain, a membrane-spanning domain, and an extracellular domain. When HGF binds to the extracellular domain of c-Met, the tyrosine kinase domain is phosphorylated, whereby the signal transduction system is activated. By this activation of the signal transduction system, cell proliferation, cell infiltration, cell movement, etc. are controlled, for example.

It has been reported that overexpression of c-Met is seen in cancer cells of many tissues such as the liver, kidney, pancreas, lung, bladder, prostate, seminal vesicle, ovary, breast, mammary gland, and digestive tracts such as the stomach and colon (Non-Patent Document 1). Thus, c-Met is attracting attention as a target and a diagnostic marker for diseases including various cancers. Under such circumstances, it has been desired to produce a substance capable of binding to c-Met and to prevent and treat the above diseases by neutralizing the action of c-Met with the substance.

CITATION LIST

Patent Document(s)

Non-Patent Document 1: Seminars in Oncology, Vol. 36, No. 2, suppl 1, 2009, pp. s52-s58

SUMMARY OF THE INVENTION

Problem to be Solved by the Invention

It is an object of the present invention to provide a nucleic acid molecule capable of binding to c-Met as a substance that can be used for clarification of the pathogenic mechanism of diseases caused by c-Met, diagnosis and treatment of the diseases, analysis of the action mechanism of the c-Met signal transduction system, and the like, and also the use of the nucleic acid molecule.

Means for Solving Problem

The present invention provides a c-Met binding nucleic acid molecule capable of binding to c-Met. The c-Met binding nucleic acid molecule includes: any one of the following polynucleotides (A1) to (A4) and (B1) to (B4):

(A1) a polynucleotide consisting of a base sequence of any one of SEQ ID NOs: 1 to 38;
(A2) a polynucleotide that is capable of binding to c-Met and consists of a base sequence obtained by substitution, deletion, addition, and/or insertion of one or more bases in the base sequence of any one of SEQ ID NOs: 1 to 38;
(A3) a polynucleotide that is capable of binding to c-Met and consists of a base sequence having an identity of at least 60% to the base sequence of any one of SEQ ID NOs: 1 to 38;
(A4) a polynucleotide that is capable of binding to c-Met and consists of a base sequence complementary to a polynucleotide that hybridizes to the polynucleotide consisting of the base sequence of any one of SEQ ID NOs: 1 to 38 under stringent conditions;
(B1) a polynucleotide consisting of a base sequence of any one of SEQ ID NOs: 39 to 76;
(B2) a polynucleotide that is capable of binding to c-Met and consists of a base sequence obtained by substitution, deletion, addition, and/or insertion of one or more bases in the base sequence of any one of SEQ ID NOs: 39 to 76;
(B3) a polynucleotide that is capable of binding to c-Met and consists of a base sequence having an identity of at least 60% to the base sequence of any one of SEQ ID NOs: 39 to 76; and
(B4) a polynucleotide that is capable of binding to c-Met and consists of a base sequence complementary to a polynucleotide that hybridizes to the polynucleotide consisting of the base sequence of any one of SEQ ID NOs: 39 to 76 under stringent conditions.

The present invention also provides a neutralizer containing the c-Met binding nucleic acid molecule of the present invention. The neutralizer neutralizes the function of c-Met by binding of the c-Met binding nucleic acid molecule with the c-Met.

The present invention also provides an inhibitor containing the c-Met binding nucleic acid molecule of the present invention. The inhibitor inhibits the function of c-Met by binding of the c-Met binding nucleic acid molecule with the c-Met.

The present invention also provides a pharmaceutical agent containing the c-Met binding nucleic acid molecule of the present invention.

The present invention also provides a composition containing the c-Met binding nucleic acid molecule of the present invention.

The present invention also provides a c-Met detection reagent for detecting c-Met. The c-Met detection reagent contains the c-Met binding nucleic acid molecule of the present invention.

Effects of the Invention

The c-Met binding nucleic acid molecule of the present invention can bind to c-Met. Thus, the c-Met binding nucleic acid molecule of the present invention inhibits the function of c-Met by binding thereto, thereby allowing the prevention and treatment of the above-described diseases caused by c-Met, for example. Furthermore, according to the c-Met binding nucleic acid molecule of the present invention, it is possible to detect c-Met by checking the presence or absence of the binding thereof with the c-Met, for example. Thus, the c-Met binding nucleic acid molecule of the present invention also allows early diagnosis of the above-described diseases. Moreover, the c-Met binding nucleic acid molecule of the present invention can be used for clarification of the function of c-Met, because, for example, experiments involving inhibition of gene transcription become possible by causing the c-Met binding nucleic acid molecule of the present invention to be expressed in cultured cells and also experiments involving inhibition of the binding of extracellular c-Met with its receptor become possible by using the c-Met binding nucleic acid molecule of the present invention. Thus, the c-Met binding nucleic acid molecule of the present invention is useful also as a novel tool for research.

Figure 1:
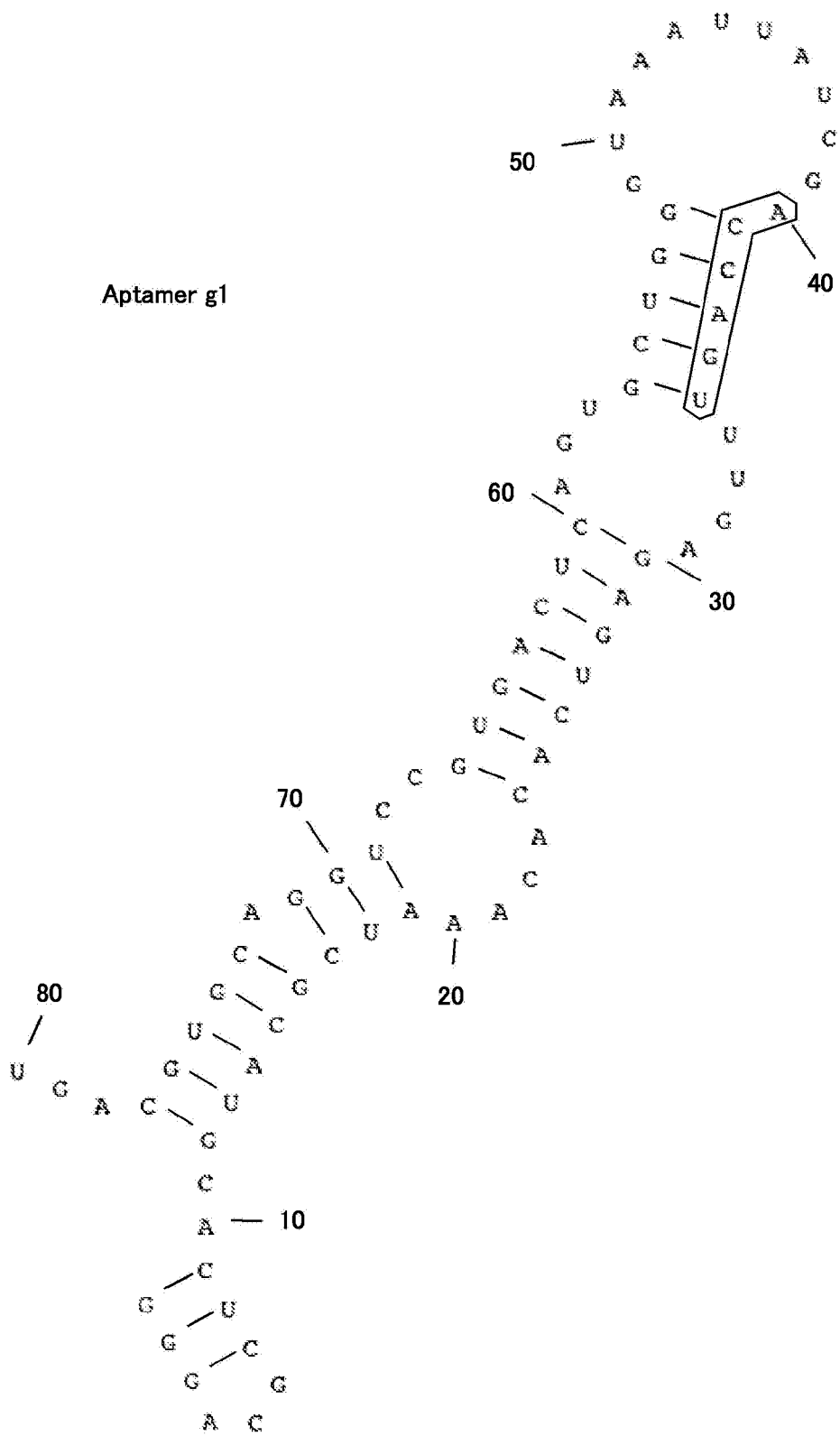
FIG. 1 is a schematic view showing the predicted secondary structure of an RNA aptamer g1 (SEQ ID NO: 39) in the present invention.

MODE FOR CARRYING OUT THE INVENTION c-Met Binding Nucleic Acid Molecule

The c-Met binding nucleic acid molecule according to the present invention is, as described above, a c-Met binding nucleic acid molecule capable of binding to c-Met, including any one of the following polynucleotides (A1) to (A4) and (B1) to (B4):
(A1) a polynucleotide consisting of a base sequence of any one of SEQ ID NOs: 1 to 38;
(A2) a polynucleotide that is capable of binding to c-Met and consists of a base sequence obtained by substitution, deletion, addition, and/or insertion of one or more bases in the base sequence of any one of SEQ ID NOs: 1 to 38;
(A3) a polynucleotide that is capable of binding to c-Met and consists of a base sequence having an identity of at least 60% to the base sequence of any one of SEQ ID NOs: 1 to 38;
(A4) a polynucleotide that is capable of binding to c-Met and consists of a base sequence complementary to a polynucleotide that hybridizes to the polynucleotide consisting of the base sequence of any one of SEQ ID NOs: 1 to 38 under stringent conditions;
(B1) a polynucleotide consisting of a base sequence of any one of SEQ ID NOs: 39 to 76;
(B2) a polynucleotide that is capable of binding to c-Met and consists of a base sequence obtained by substitution, deletion, addition, and/or insertion of one or more bases in the base sequence of any one of SEQ ID NOs: 39 to 76;
(B3) a polynucleotide that is capable of binding to c-Met and consists of a base sequence having an identity of at least 60% to the base sequence of any one of SEQ ID NOs: 39 to 76; and
(B4) a polynucleotide that is capable of binding to c-Met and consists of a base sequence complementary to a polynucleotide that hybridizes to the polynucleotide consisting of the base sequence of any one of SEQ ID NOs: 39 to 76 under stringent conditions.

In the present invention, "capable of binding to c-Met" also is referred to as, for example, "having a binding ability to c-Met" or "having a binding activity to c-Met (a c-Met binding activity)". The c-Met binding nucleic acid molecule of the present invention specifically binds to c-Met, for example. The binding of the c-Met binding nucleic acid molecule with c-Met can be determined by surface plasmon resonance analysis of intermolecular interaction or the like, for example. The analysis can be carried out using BIACORE X (trade name, GE Healthcare Ltd.), for example.

Regarding c-Met in the present invention, the amino acid sequence of the isoform b (SEQ ID NO: 80) is disclosed under NCBI Accession No. 42741655, for example.

The c-Met binding nucleic acid molecule of the present invention also is referred to as a "c-Met aptamer", for example. The nucleic acid molecule of the present invention may consist of or include any one of the polynucleotides (A1) to (A4) and (B1) to (B4), for example.

A nucleic acid molecule including the polynucleotide (A1) will be described. Hereinafter, the nucleic acid molecule including the polynucleotide (A1) is referred to as a "c-Met binding nucleic acid molecule (A1)". In the c-Met binding nucleic acid molecule (A1), a base sequence of any one of SEQ ID NOs: 1 to 38 also is referred to as a "base sequence (A1)".
(A1) a polynucleotide consisting of a base sequence of any one of SEQ ID NOs: 1 to 38

The name indicated in front of each of the following sequence identification numbers also can be used to refer to a polynucleotide consisting of the base sequence (A1) and the c-Met binding nucleic acid molecule (A1) including the polynucleotide of the base sequence (A1).

```
g1
                                       (SEQ ID NO: 1)
acacacugagaguuugaccagcuauuaaaugggucgugac g2
                                       (SEQ ID NO: 2)
acccuggcgaucuccggccggauacgggagaacgagguac g3
                                       (SEQ ID NO: 3)
gggcgaaacugucgugacacgguuugacaugccggccuua g4
                                       (SEQ ID NO: 4)
uaccgugauucggggugguauccgguggacauccaggucg
```

-continued g5
(SEQ ID NO: 5)
gcccaacgaacauuuugaguuuccaggcagcucauagaca g6
(SEQ ID NO: 6)
uccaggguguggcgagccacuguaagagucgccgugaggau g7
(SEQ ID NO: 7)
cuugaagucaaggguagagugaccaugcagcucguagaca g8
(SEQ ID NO: 8)
gggcacuuaaaaccagaccgugauuugcgguuggucucgc g9
(SEQ ID NO: 9)
gaugucucaauuggucgugauugugcugaccacacgaacc g10
(SEQ ID NO: 10)
acacagcucugauggucgugauuagguugaccaccuaccu g11
(SEQ ID NO: 11)
guuuagguggcaucgaccuucaugaaacgggugcacaggc g12
(SEQ ID NO: 12)
cgcggccauccggcguuuggaacgggaugua caccugaca g13
(SEQ ID NO: 13)
ucacucggacagccggagcgaaacgggcuguguaagacug g14
(SEQ ID NO: 14)
ucaucgggacaucggauggaacggguguc aagaagcgugu g15
(SEQ ID NO: 15)
gacgcgggccaccggcuagcgacgggugsuaaagggcuug g16
(SEQ ID NO: 16)
ccgcuaccgggugcaacgggua gacuguaaccaggugaua g17
(SEQ ID NO: 17)
agugauggccggcuggagaaacgggccacucgauccagg g18
(SEQ ID NO: 18)
ggcacccuauaggauucagcccuaacccgguguugugaa g19
(SEQ ID NO: 19)
guagccgugauugg guuggcugcccacaauuauccaggac g20
(SEQ ID NO: 20)
acguguggcgaacuucggcccgaacgggaguaacugca g21
(SEQ ID NO: 21)
ccuuggugucauccgaccaaauuagaacgggaugaggaag g22
(SEQ ID NO: 22)
gcguguuucuucauuucgacgcuggccaacggaaaugcaa g23
(SEQ ID NO: 23)
augggagugcgccucggcucuaacggagguaugcacguca g24
(SEQ ID NO: 24)
gaguugucgcacagcgacucgaaaauaaucuguccgacac g25
(SEQ ID NO: 25)
uagcaacaguucccagaggugaucaggcagccuuaagaca g26
(SEQ ID NO: 26)
gcuccaccaggguguagcuagccuguagacaucaguagca g27
(SEQ ID NO: 27)
ccuaugcagaccgacauccggguauacgggaugaugcgac g28
(SEQ ID NO: 28)
ccuggggguuccgcaggaaucgggaacuagauuggugguc g29
(SEQ ID NO: 29)
acgagccgugauuggguuggcaacccugcuuaugugagga g30
(SEQ ID NO: 30)
aaauugccgggaucggguguggcgaccaugcggcgugcau g31
(SEQ ID NO: 31)
agagucuaugccgugagugagggguggcgccucgacugcca g32
(SEQ ID NO: 32)
acaagaccgggauggggguuggucacacacaaagacugaa g33
(SEQ ID NO: 33)
acuuuuggcgaucuccggccggauacgggagaacgaggua g34
(SEQ ID NO: 34)
uuuggugaauuccgaccauuuugcaaacgggauacgggac g35
(SEQ ID NO: 35)
gauuugugugauacccgacacucuaacggggguagcagggc g36
(SEQ ID NO: 36)
cuugauuggucgcaaccggacaaggacggguugaugcagu g37
(SEQ ID NO: 37)
gguuugcuccgaccgacuaaagggagccucugucacgagu g38
(SEQ ID NO: 38)
ccaggagcauuagaccggggaaagaaggaguaccgucugg The c-Met binding nucleic acid molecule (A1) may include or consist of the polynucleotide consisting of the base sequence (A1), for example.

In the case where the c-Met binding nucleic acid molecule (A1) includes the polynucleotide consisting of the base sequence (A1), it may further include a Y region and/or a Y' region, with the base sequence (A1) being an X region, for example. In the c-Met binding nucleic acid molecule (A1), the X region, the Y region, and the Y' region preferably are linked in the following order from the 5' side, for example: the Y region, the X region, and the Y' region. The Y region is not particularly limited, and may be a sequence consisting of or including the base sequence of SEQ ID NO: 77 or 78, for example. Also, the Y' region is not particularly limited, and may be a sequence consisting of or including the base sequence of SEQ ID NO: 79, for example. It is to be noted that these sequences are merely illustrative and do not limit the present invention by any means.

```
                                                    (SEQ ID NO: 77)
gggacgcucacguacgcuaa (SEQ ID NO: 78)
acgcucacguacgcuaa (SEQ ID NO: 79)
ucagugccuggacgugcagu
```

In the c-Met binding nucleic acid molecule (A1), the Y region preferably is bound to the 5' side of the base sequence (A1), for example. Also, in the c-Met binding nucleic acid molecule (A1), the Y' region preferably is bound to the 3' side of the base sequence (A1), for example. The base sequence (A1) and the Y region, and the base sequence (A1) and the Y' region may be bound to each other directly or via an intervening sequence, for example.

The Y region and the Y' region are not particularly limited. Each of the Y region and the Y' region preferably has a primer binding sequence to which a primer can anneal, a polymerase recognition sequence that can be recognized by polymerase, and the like, for example. When a large number of nucleic acid molecules need to be produced, for example, more efficient production is possible by amplification according to a nucleic acid amplification method, rather than by chemical synthesis such as described above. Considering the case where the c-Met binding nucleic acid molecule is amplified by the nucleic acid amplification method, it is preferable that the c-Met binding nucleic acid molecule has a primer binding sequence to which a primer can hybridize, a polymerase recognition sequence recognized by polymerase, and the like, for example. The c-Met binding nucleic acid molecule preferably has the primer binding sequence and the polymerase recognition sequence in at least one of a region upstream of the 5' side of the X region (i.e., the Y region) and a region downstream of the 3' side of the X region (i.e., the Y' region), for example. The polymerase recognition region can be determined as appropriate depending on the kind of polymerase to be used in the nucleic acid amplification, for example. In the case where the c-Met binding nucleic acid molecule is RNA, the polymerase recognition sequence preferably is, for example, a DNA-dependent RNA polymerase recognition sequence (hereinafter also referred to as "RNA polymerase recognition sequence"), and specific examples thereof include a T7 promoter, which is a recognition sequence of T7 RNA polymerase. In the case where the c-Met binding nucleic acid molecule is RNA, for example, the Y region on the 5' side preferably has the RNA polymerase recognition sequence and the primer binding sequence (hereinafter also referred to as a "5' side primer region") in this order. Preferably, the X region is linked to the 3' side of the Y region. Furthermore, the Y' region preferably is linked to the 3' side of the X region, and the Y' region preferably has the primer binding sequence (hereinafter also referred to as a "3' side primer region"). The 5' side primer region in the RNA preferably is, for example, a sequence complementary to a 3' side region in a DNA antisense strand synthesized with the RNA as a template, i.e., the same sequence as a primer that can bind to the 3' side region in the antisense strand. The c-Met binding nucleic acid molecule may further include a region that assists the binding to c-Met, for example. In the c-Met binding nucleic acid molecule, the Y region and the X region, and the X region and the Y' region may be adjacent to each other directly or indirectly via an intervening sequence, for example.

The number of bases in the Y region and the number of bases in the Y' region are not particularly limited, and both are, for example, 10 to 50, preferably 15 to 40, more preferably 20 to 37, and still more preferably 20 to 30.

When the c-Met binding nucleic acid molecule (A1) includes the base sequence (A1), the c-Met binding nucleic acid molecule (A1) may be a nucleic acid molecule that includes or consists of a polynucleotide consisting of the base sequence of any one of SEQ ID NOs: 39 to 76, for example. The base sequences of SEQ ID NOs: 39 to 76 shown below include the base sequences (A1) of SEQ ID NOs: 1 to 38, respectively. The underlined regions in the base sequences of SEQ ID NOs: 39 to 76 correspond to the base sequences of SEQ ID NOs: 1 to 38, respectively. The names indicated in front of the following sequence identification numbers also can be used to refer to polynucleotides consisting of the base sequences of SEQ ID NOs: 39 to 76 and the c-Met binding nucleic acid molecules (A1) respectively including these polynucleotides.

```
g1
                                                                                            (SEQ ID NO: 39)
gggacgcucacguacgcuaaacacacugagaguuugaccagcuauuaaaugggucgugacucagugccuggacgugcagu g2
                                                                                            (SEQ ID NO: 40)
gggacgcucacguacgcuaaacccuggcgaucuccggccggauacgggagaacgagguacucagugccuggacgugcagu g3
                                                                                            (SEQ ID NO: 41)
gggacgcucacguacgcuaagggcgaaacugucgugacacgguuugacaugccggccuuaucagugccuggacgugcagu g4
                                                                                            (SEQ ID NO: 42)
gggacgcucacguacgcuaauaccgugauucggguggauccgguggacauccaggucgucagugccuggacgugcagu g5
                                                                                            (SEQ ID NO: 43)
gggacgcucacguacgcuaagcccaacgaacauuuugaguuuccaggcagcucauagacaucagugccuggacgugcagu g6
                                                                                            (SEQ ID NO: 44)
gggacgcucacguacgcuaauccaggguguggcgagccacuguaagagucgccgugaggauucaaugccuggacgugcagu g7
                                                                                            (SEQ ID NO: 45)
gggacgcucacguacgcuaacuugaagucaaggguagagugaccaugcagcucguagacaucagugccuggacgugcagu
``` g8

(SEQ ID NO: 46)

gggacgcucacguacgcuaagggcacuuaaaaccagaccgugauuugcgguuggucucgcucagugccuggacgugcagu g9

(SEQ ID NO: 47)

gggacgcucacguacgcuaagaugucucaauuggucgugauugugcugaccacacgaaccucagugccuggacgugcagu g10

(SEQ ID NO: 48)

gggacgcucacguacgcuaaacacagcucugauggucgugauuagguugaccaccuaccuucagugccuggacgugcagu g11

(SEQ ID NO: 49)

gggacgcucacguacgcuaaguuuaggugcaucgaccuucaugaaacgggugcacaggcucagugccuggacgugcagu g12

(SEQ ID NO: 50)

gggacgcucacguacgcuaacgcggccauccggcguuggaacgggauguacaccugacaucagugccuggacgugcagu g13

(SEQ ID NO: 51)

gggacgcucacguacgcuaaucacucggacagccggagcgaaacgggcuguguaagacugucagugccuggacgugcagu g14

(SEQ ID NO: 52)

gggacgcucacguacgcuaaucaucgggacaucggauggaacgggugucaagaagcguguucagugccuggacgugcagu g15

(SEQ ID NO: 53)

gggacgcucacguacgcuaagacgcgggccaccggcuagcgacgggugguaaagggcuugucagugccuggacgugcagu g16

(SEQ ID NO: 54)

gggacgcucacguacgcuaaccgcuaccgggugcaacggguagacuuaaccaggugauaucagugccuggacgugcagu g17

(SEQ ID NO: 55)

gggacgcucacguacgcuaaagugauggccggcuggagaaacgggccacucgauccaggucagugccuggacgugcagu g18

(SEQ ID NO: 56)

gggacgcucacguacgcuaaggcacccuauaggauucagccccuaacccggguguugugaaucagugccuggacgugcagu g19

(SEQ ID NO: 57)

gggacgcucacguacgcuaaguagccgugauuggguuggcugcccacaauuauccaggacucagugccuggacgugcagu g20

(SEQ ID NO: 58)

gggacgcucacguacgcuaaacguuguggcgaacuucggcccgaacgggaguaacugcaucagugccuggacgugcagu g21

(SEQ ID NO: 59)

gggacgcucacguacgcuaaccuuggugucauccgaccaaauuagaacgggaugaggaagucagugccuggacgugcagu g22

(SEQ ID NO: 60)

gggacgcucacguacgcuaagcguguuucuucauuucgacgcuggccaacggaaaugcaaucagugccuggacgugcagu g23

(SEQ ID NO: 61)

aggacgcucacguacgcuaaaugggagugcgccucggcucuaacggagguaugcacgucaucagugccuggacgugcagu g24

(SEQ ID NO: 62)

gggacgcucacguacgcuaagaguugucgcacagcgacucgaaaauaaucuguccgacacucagugccuggacgugcagu g25

(SEQ ID NO: 63)

gggacgcucacguacgcuaauagcaacaguucccagaggugaucaggcagccuuaagacaucagugccuggacgugcagu g26

(SEQ ID NO: 64)

gggacgcucacguacgcuaagcuccaccaggguguagcuagccuguagacaucaguagcaucagugccuggacgugcagu g27

(SEQ ID NO: 65)

gggacgcucacguacgcuaaccuaugcagaccgacauccgggauacgggaugaugcgacucagugccuggacgugcagu

```
g28
                                                             (SEQ ID NO: 66)
gggacgcucacguacgcuaaccugggguuccgcaggaaucgggaacuagauugguggucucagugccuggacgugcagu g29
                                                             (SEQ ID NO: 67)
gggacgcucacguacgcuaaacgagccugauuggguuggcaacccugcuuaugugagga ucagugccuggacgugcagu g30
                                                             (SEQ ID NO: 68)
gggacgcucacguacgcuaaaaauugccgggaucuggugugg cgaccaugcggcgugcauucagugccuggacgugcagu g31
                                                             (SEQ ID NO: 69)
gggacgcucacguacgcuaaagagucuaugccgugaguga ggguggcgccucgacugccaucagugccuggacgugcagu g32
                                                             (SEQ ID NO: 70)
gggacgcucacguacgcuaaacaagaccgggauggggguuggucacacacaaagacugaaucagugccuggacgugcagu g33
                                                             (SEQ ID NO: 71)
gggacgcucacguacgcuaaacuuuggcgaucuccggccggauacgggagaacgagguaucagugccuggacgugcagu g34
                                                             (SEQ ID NO: 72)
gggacgcucacguacgcuaauuuggugaauuccgaccauuuugcaaacgggauacgggacucagugccuggacgugcagu g35
                                                             (SEQ ID NO: 73)
gggacgcucacguacgcuaagauuuguaugauacccgacacucuaacggggu agcagggcucagugccuggacgugcagu g36
                                                             (SEQ ID NO: 74)
gggacgcucacguacgcuaacuugauuggucgcaaccggacaaggacggguugaugcaguucagugccuggacgugcagu g37
                                                             (SEQ ID NO: 75)
gggacgcucacguacgcuaaggu uugcuccgaccgacuaaagggagccucuguca cgaguucagugccuggacgugcagu g38
                                                             (SEQ ID NO: 76)
gggacgcucacguacgcuaaccaggagcauuagaccggggaaagaaggaguaccgucuggucagugccuggacgugcagu
```

Figure 10:
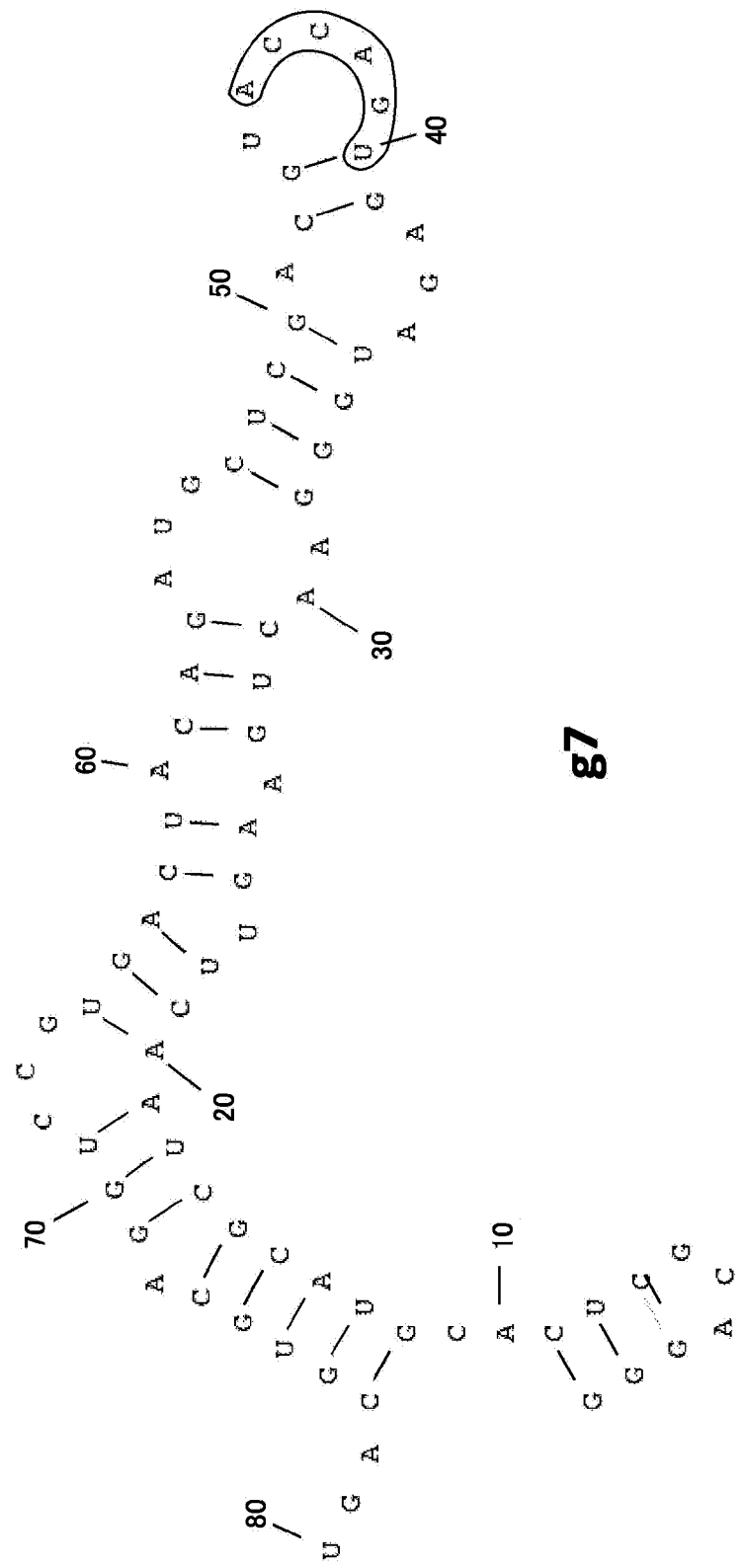
FIG. 10 is a schematic view showing the predicted secondary structure of an RNA aptamer g7 (SEQ ID NO: 45) in the present invention.

The predicted secondary structure of g1 (SEQ ID NO: 39) is shown in FIG. 1, and the predicted secondary structure of g7 (SEQ ID NO: 45) is shown in FIG. 10. In FIGS. 1 and 10, the region surrounded with a line is an example of a conserved region among the above-described c-Met binding nucleic acid molecules.

The total number of bases in the c-Met binding nucleic acid molecule (A1) is not particularly limited, and is, for example, 20 to 160, preferably 30 to 120, and more preferably 40 to 100.

Next, a nucleic acid molecule including the polynucleotide (A2) will be described. Hereinafter, the nucleic acid molecule including the polynucleotide (A2) is referred to as a "c-Met binding nucleic acid molecule (A2)". In the c-Met binding nucleic acid molecule (A2), substitution, deletion, addition, and insertion are hereinafter referred to as "modification", and the following base sequence obtained by the modification also is referred to as a "base sequence (A2)".

(A2) a polynucleotide that is capable of binding to c-Met and consists of a base sequence obtained by substitution, deletion, addition, and/or insertion of one or more bases in the base sequence of any one of SEQ ID NOs: 1 to 38

The c-Met binding nucleic acid molecule (A2) may include or consist of the modified base sequence (A2), for example.

In the polynucleotide (A2), "one or more" is not particularly limited, as long as the polynucleotide (A2) can bind to c-Met. The term "one or more" means, for example, 1 to 5, preferably 1 to 4, more preferably 1 to 3, still more preferably 1 or 2, and particularly preferably 1, in the base sequence (A1). Also, the term "one or more" means, for example, 1 to 5, preferably 1 to 4, more preferably 1 to 3, still more preferably 1 or 2, and particularly preferably 1, in the full length sequence of the c-Met binding nucleic acid molecule (A1).

The total number of bases in the c-Met binding nucleic acid molecule (A2) is not particularly limited, and is, for example, 20 to 160, preferably 30 to 120, and more preferably 40 to 100.

Similarly to the c-Met binding nucleic acid molecule (A1), the c-Met binding nucleic acid molecule (A2) may further include the Y region and/or the Y' region, for example. In this case, for example, the Y region and the Y' region are as described above, with the base sequence (A2) being the X region.

The polynucleotide (A2) is not particularly limited, and specific examples thereof include a polynucleotide consisting of the base sequence from the 4th base on the 5' side to the terminal base on the 3' side in the base sequence (A1). In other words, the polynucleotide (A2) may be a polynucleotide obtained by deletion of ggg from the 5' end of the base sequence (A1), for example.

Next, a nucleic acid molecule including the polynucleotide (A3) will be described. Hereinafter, the nucleic acid molecule including the polynucleotide (A3) is referred to as a "c-Met binding nucleic acid molecule (A3)". In the c-Met binding nucleic acid molecule (A3), a base sequence having the following identity also is referred to as a "base sequence (A3)".

(A3) a polynucleotide that is capable of binding to c-Met and consists of a base sequence having an identity of at least 60% to the base sequence of any one of SEQ ID NOs: 1 to 38

The c-Met binding nucleic acid molecule (A3) may include or consist of a polynucleotide consisting of the base sequence (A3) having the above-described identity, for example.

In the polynucleotide (A3), the identity to the base sequence (A1) is, for example, at least 70%, preferably at least 80%, more preferably at least 90%, still more preferably at least 95%, and particularly preferably at least 99%. The identity may be such that, for example, the full length sequence of the c-Met binding nucleic acid molecule (A3) has an identity of at least 70%, preferably at least 80%, more preferably at least 90%, still more preferably at least 95%, and particularly preferably at least 99% to the full length sequence of the c-Met binding nucleic acid molecule (A1). The identity can be calculated by using BLAST or the like under default conditions, for example.

The total number of bases in the c-Met binding nucleic acid molecule (A3) is not particularly limited, and is, for example, 20 to 160, preferably 30 to 120, and more preferably 40 to 100.

Similarly to the c-Met binding nucleic acid molecule (A1), the c-Met binding nucleic acid molecule (A3) may further include the Y region and/or the Y' region, for example. In this case, for example, the Y region and the Y' region are as described above, with the base sequence (A3) being the X region.

Next, a nucleic acid molecule including the polynucleotide (A4) will be described. Hereinafter, the nucleic acid molecule including the polynucleotide (A4) is referred to as a "c-Met binding nucleic acid molecule (A4)". In the c-Met binding nucleic acid molecule (A4), the following complementary base sequence also is referred to as a "base sequence (A4)".
(A4) a polynucleotide that is capable of binding to c-Met and consists of a base sequence complementary to a polynucleotide that hybridizes to the polynucleotide consisting of the base sequence of any one of SEQ ID NOs: 1 to 38 under stringent conditions The c-Met binding nucleic acid molecule (A4) may include or consist of a polynucleotide consisting of the base sequence (A4), for example. Also, the polynucleotide (A4) may be a polynucleotide that is capable of binding c-Met and hybridizes to the polynucleotide consisting of the base sequence (A1) under stringent conditions, for example.

In the polynucleotide (A4), "hybridization under stringent conditions" means hybridization under experimental conditions well known to those skilled in the art, for example. Specifically, the term "stringent conditions" refers to conditions such that a hybrid formed is identified after carrying out hybridization at 60° C. to 68° C. in the presence of 0.7 to 1 mol/L NaCl and then carrying out washing at 65° C. to 68° C. using a 0.1- to 2-fold SSC solution. Note here that 1×SSC is composed of 150 mmol/L NaCl and 15 mmol/L sodium citrate, for example. The c-Met binding nucleic acid molecule (A4) may be a nucleic acid molecule that is capable of binding to c-Met and includes a base sequence that hybridizes to the full length sequence of the c-Met binding nucleic acid molecule (A1) under stringent conditions, for example.

The total number of bases in the c-Met binding nucleic acid molecule (A4) is not particularly limited, and is, for example, 20 to 160, preferably 30 to 120, and more preferably 40 to 100.

Similarly to the c-Met binding nucleic acid molecule (A1), the c-Met binding nucleic acid molecule (A4) may further include the Y region and/or the Y' region, for example. In this case, for example, the Y region and the Y' region are as described above, with the base sequence (A4) being the X region.

Next, a nucleic acid molecule including the polynucleotide (B1) will be described. Hereinafter, the nucleic acid molecule including the polynucleotide (B1) is referred to as a "c-Met binding nucleic acid molecule (B1)". In the c-Met binding nucleic acid molecule (B1), a base sequence of any one of SEQ ID NOs: 39 to 76 also is referred to as a "base sequence (B1)".
(B1) a polynucleotide consisting of a base sequence of any one of SEQ ID NOs: 39 to 76

The base sequences of SEQ ID NOs: 39 to 76 are as described above. The names indicated in front of the sequence identification numbers listed above also can be used to refer to polynucleotides consisting of the base sequences (B1) of SEQ ID NOs: 39 to 76, and the c-Met binding nucleic acid molecules (B1) respectively including the base sequences (B1).

The c-Met binding nucleic acid molecule (B1) may include or consist of a polynucleotide consisting of the base sequence (B1), for example.

The total number of bases in the c-Met binding nucleic acid molecule (B1) is not particularly limited. The upper limit of its full length is, for example, 160 bases, preferably 120 bases, and more preferably 100 bases.

Similarly to the c-Met binding nucleic acid molecule (A1), the c-Met binding nucleic acid molecule (B1) may further include the Y region and/or the Y' region, for example. In this case, the Y region and the Y' region are as described above, with the base sequence (B1) being the X region, for example.

In particular, the c-Met binding nucleic acid molecule (B1) preferably is a nucleic acid molecule including the following polynucleotide (b1), for example. Hereinafter, the nucleic acid molecule including the polynucleotide (b1) also is referred to as a "c-Met binding nucleic acid molecule (b1)". The c-Met binding nucleic acid molecule (b1) may include or consist of a polynucleotide consisting of the base sequence of SEQ ID NO: 39, for example.
(b1) a polynucleotide consisting of the base sequence of SEQ ID NO: 39

Next, a nucleic acid molecule including the polynucleotide (B2) will be described. Hereinafter, the nucleic acid molecule including the polynucleotide (B2) is referred to as a "c-Met binding nucleic acid molecule (B2)". In the c-Met binding nucleic acid molecule (B2), substitution, deletion, addition, and insertion are hereinafter referred to as "modification", and the following base sequence obtained by the modification also is referred to as a "base sequence (B2)".
(B2) a polynucleotide that is capable of binding to c-Met and consists of a base sequence obtained by substitution, deletion, addition, and/or insertion of one or more bases in the base sequence of any one of SEQ ID NOs: 39 to 76

The c-Met binding nucleic acid molecule (B2) may include or consist of the modified base sequence (B2), for example.

In the polynucleotide (B2), "one or more" is not particularly limited, as long as the polynucleotide (B2) can bind to c-Met. The number of substituted bases is, for example, 1 to 5, preferably 1 to 4, more preferably 1 to 3, still more preferably 1 or 2, and particularly preferably 1 in the base sequence (B1). The number of the added or inserted bases is, for example, 1 to 5, preferably 1 to 4, more preferably 1 to 3, still more preferably 1 or 2, and particularly preferably 1 in the base sequence (B1). The number of the deleted bases is, for example, 1 to 40, 1 to 20, 1 to 4, 1 to 3, or 2 or 1 in the base sequence (B1).

The length of the c-Met binding nucleic acid molecule (B2) is not particularly limited, and the full length thereof is, for example, 20- to 160-mer, preferably 30- to 120-mer, and more preferably 40- to 100-mer.

Among various c-Met binding nucleic acid molecules corresponding to the c-Met binding nucleic acid molecule (B2), for example, those capable of binding to c-Met and including a polynucleotide consisting of a base sequence obtained by deletion of one or more bases in the base sequence (B1) also can be referred to as a nucleic acid molecule obtained by truncating the c-Met binding nucleic acid molecule (B1). The truncated nucleic acid molecule also is referred to as a "truncated c-Met binding nucleic acid molecule (B2)".

In the truncated c-Met binding nucleic acid molecule (B2), the base sequence obtained by the deletion also is referred to as a "truncated base sequence (B2)". The truncated base sequence (B2) may further include, for example, in addition to the deletion of one or more bases in the base sequence (B1), substitution, addition, and/or insertion of one or more bases in the same, for example. The truncated c-Met binding nucleic acid molecule may include or consist of a polynucleotide consisting of the truncated base sequence (B2), for example.

(b2) a polynucleotide that is capable of binding to c-Met and consists of a base sequence obtained by deletion of one or more bases in the base sequence of SEQ ID NO: 39

A base sequence obtained by deletion of one or more bases in the base sequence of SEQ ID NO: 39 hereinafter also is referred to as a "deleted base sequence". The deleted base sequence may be a base sequence of any one of SEQ ID NOs: 81 to 89, for example. These base sequences are shown in Table 1 below. In Table 1, each base sequence is shown in alignment with the base sequence of SEQ ID NO: 39. In each base sequence, deleted parts as compared with the base sequence of SEQ ID NO: 39 are shown as blanks. The names shown in Table 1 below also can be used to refer to polynucleotides consisting of the base sequences of SEQ ID NO: 81 to 89 and the truncated c-Met binding nucleic acid molecules (b2) respectively including these polynucleotides.

TABLE 1

| Aptamer | Sequence | SEQ No. |
|---|---|---|
| g1 | GGGACGCUCACGUACGCUAA ACACACUGAGAGUUUGACCAGCUAUUAAAUGGGUCGUGAC UCAGUGCCUGGACGUGCAGU | 39 |
| g1-u5del | GGG     CACGUACGCUAA ACACACUGAGAGUUUGACCAGCUAUUAAAUGGGUCGUGAC UCAGUGCCUGGACGUGCAG | 81 |
| g1-u100del | GGG          ACGCUAA ACACACUGAGAGUUUGACCAGCUAUUAAAUGGGUCGUGAC UCAGUGCCUGGACGUGC | 82 |
| g1-u20del | GGG                  CACUGAGAGUUUGACCAGCUAUUAAAUGGGUCGUGAC UCAGUGCCUGGACGUG | 83 |
| g1-d5del | GGGACGCUCACGUACGCUAA ACACACUGACACUUUGACCAGCUAUUAAAUGGGCUCGUGAC UCAGUCCCUGGACGU | 84 |
| g1-d10del | GGGACGCUCACGUACGCUAA ACACACUGAGAGUUUGACCAGCUAUUAAAUGGGUCGUGAC UCAGUGCCUG | 85 |
| g1-u20del-d14del | GGG                  CACUGAGAGUUUGACCAGCUAUUAAAUGGGUCGUGAC UCAGUG | 86 |
| g1-u21del-d15del | GGG                   ACUGAGAGUUUGACCAGCUAUUAAAUGGGUCGUGAC UCAGU | 87 |
| g1-u22del-d16del | GGG                    CUGAGAGUUUGACCAGCUAUUAAAUGGGUCGUGAC UCAG | 88 |
| g1-u23del-d17del | GGG                     UGAGAGUUUGACCAGCUAUUAAAUGGGUCGUGAC UCA | 89 |

The truncated c-Met binding nucleic acid molecule (B2) may include or consist of the polynucleotide consisting of the truncated base sequence (B2) obtained by the deletion, as described above.

The polynucleotide consisting of the truncated base sequence (B2) is not particularly limited, and specific examples thereof include a polynucleotide consisting of a base sequence from the 4th base on the 5' side to the terminal base on the 3' side in the base sequence (B1). In other words, the polynucleotide consisting of the base sequence (B2) may be a polynucleotide obtained by deletion of ggg in the 5' end of the base sequence (B1), for example.

The length of the truncated c-Met binding nucleic acid molecule (B2) is not particularly limited, and the full length thereof is, for example, 20 to 160-mer, preferably 30 to 120-mer, and more preferably 40 to 100-mer.

Similarly to the c-Met binding nucleic acid molecule (B1), the c-Met binding nucleic acid molecule (B2) may further include the Y region and/or the Y' region, for example. In this case, the Y region and the Y' region are as described above, with the base sequence (B2) being the X region, for example.

In particular, the truncated c-Met binding nucleic acid molecule (B2) preferably is a nucleic acid molecule including the following polynucleotide (b2), for example. Hereinafter, the nucleic acid molecule including the polynucleotide (b2) also is referred to as a "truncated c-Met binding nucleic acid molecule (b2)". The c-Met binding nucleic acid molecule (b2) may include or consist of a polynucleotide consisting of the base sequence of SEQ ID NO: 39, for example.

The truncated c-Met binding nucleic acid molecule (b2) may include or consist of a polynucleotide consisting of the base sequence of any one of SEQ ID NOs: 81 to 89, for example.

The truncated base sequence (B2) is not particularly limited, and specific examples thereof include a polynucleotide consisting of the base sequence from the 4th base on the 5' side to the terminal base on the 3' side in each of the base sequences (b2) of SEQ ID NO: 39 and SEQ ID NOs: 81 to 89. In other words, the truncated base sequence (B2) may be a polynucleotide obtained by deletion of ggg in the 5' end of any one of the base sequences (b2) of SEQ ID NO: 39 and SEQ ID NOs: 81 to 89, for example.

The length of the truncated c-Met binding nucleic acid molecule (b2) is not particularly limited, and the full length thereof is, for example, 20 to 160-mer, preferably 30 to 120-mer, and more preferably 40 to 100-mer.

Similarly to the c-Met binding nucleic acid molecule (B1), the c-Met binding nucleic acid molecule (b2) may further include the Y region and/or the Y' region, for example. In this case, the Y region and the Y' region are as described above, with the base sequence (b2) being the X region, for example.

Next, a nucleic acid molecule including the polynucleotide (B3) will be described. Hereinafter, the nucleic acid molecule including the polynucleotide (B3) is referred to as a "c-Met binding nucleic acid molecule (B3)". In the c-Met binding nucleic acid molecule (B3), a base sequence having the identity described below also is referred to as a "base sequence (B3)".

(B3) a polynucleotide that is capable of binding to c-Met and consists of a base sequence having an identity of at least 60% to the base sequence of any one of SEQ ID NOs: 38 to 76

The c-Met binding nucleic acid molecule (B3) may include or consist of a polynucleotide consisting of the base sequence (B3) having the above-described identity.

In the polynucleotide (B3), the identity to the base sequence (B1) is, for example, at least 70%, preferably at least 80%, more preferably at least 90%, still more preferably at least 95%, and particularly preferably at least 99%. The identity may be such that, for example, the full length sequence of the c-Met binding nucleic acid molecule (B3) has an identity of at least 70%, preferably at least 80%, more preferably at least 90%, still more preferably at least 95%, and particularly preferably at least 99% to the full length sequence of the c-Met binding nucleic acid molecule (B1). The identity can be calculated by using BLAST or the like under default conditions, for example.

The total number of bases in the c-Met binding nucleic acid molecule (B3) is not particularly limited, and is, for example, 20 to 160, preferably 30 to 120, and more preferably 40 to 100.

Similarly to the c-Met binding nucleic acid molecule (B1), the c-Met binding nucleic acid molecule (B3) may further include the Y region and/or the Y' region, for example. In this case, for example, the Y region and the Y' region are as described above, with the base sequence (B3) being the X region.

Next, a nucleic acid molecule including the polynucleotide (B4) will be described. Hereinafter, the nucleic acid molecule including a polynucleotide (B4) is referred to as a "c-Met binding nucleic acid molecule (B4)". In the c-Met binding nucleic acid molecule (B4), the following complementary base sequence also is referred to as a "base sequence (B4)". (B4) a polynucleotide that is capable of binding to c-Met and consists of a base sequence complementary to a polynucleotide that hybridizes to the polynucleotide consisting of the base sequence of any one of SEQ ID NOs: 38 to 76 under stringent conditions.

The c-Met binding nucleic acid molecule (B4) may include or consist of a polynucleotide consisting of the base sequence (B4), for example. Also, the polynucleotide (B4) may be a polynucleotide that is capable of binding to c-Met and hybridizes to the polynucleotide consisting of the base sequence (B1) under stringent conditions, for example.

In the polynucleotide (B4), "hybridization under stringent conditions" means hybridization under experimental conditions well known to those skilled in the art, for example. The term "stringent conditions" is as described above. The c-Met binding nucleic acid molecule (B4) may be a nucleic acid molecule that is capable of binding to c-Met and includes a base sequence that hybridizes to the full length sequence of the c-Met binding nucleic acid molecule (B1) under stringent conditions, for example.

The total number of bases in the c-Met binding nucleic acid molecule (B4) is not particularly limited, and is, for example, 20 to 160, preferably 30 to 120, and more preferably 40 to 100.

Similarly to the c-Met binding nucleic acid molecule (B1), the c-Met binding nucleic acid molecule (B4) may further include the Y region and/or the Y' region, for example. In this case, for example, the Y region and the Y' region are as described above, with the base sequence (B4) being the X region.

The nucleic acid molecule of the present invention may include any one of the polynucleotides (A1) to (A4) and (B1) to (B4), or a plurality of these polynucleotides, for example. In the latter case, the two or more polynucleotides preferably are linked together to form a single strand polynucleotide. The sequences of the plurality of polynucleotides may be linked with each other directly or indirectly via a linker(s), for example. Preferably, the sequences of the plurality of polynucleotides are linked with each other directly or indirectly at their ends. The sequences of the plurality of polynucleotides may be the same or different, but preferably are the same, for example. When the nucleic acid molecule of the present invention includes the sequences of the plurality of polynucleotides, the number of the sequences is not particularly limited, and is, for example, two or more, preferably two.

The length of the linker is not particularly limited, and is, for example, 1- to 80-mer, preferably 5- to 60-mer, more preferably 5- to 40-mer, and still more preferably 5- to 30-mer.

The c-Met binding nucleic acid molecule of the present invention preferably is a single-stranded nucleic acid, for example. It is preferable that the single-stranded nucleic acid can form a stem structure and a loop structure by self-annealing, for example. It is preferable that the polynucleotide can form a stem structure, a loop structure, an internal loop structure, and/or a bulge structure, for example.

In the case where the c-Met binding nucleic acid molecule of the present invention is, for example, a double-stranded nucleic acid, it is preferable that, for example, one of the single strands is any one of the nucleic acid molecules (A1) to (A4) and (B1) to (B4), and the other single strand is a nucleic acid molecule consisting of or including a base sequence complementary to the any one of the nucleic acid molecules (A1) to (A4) and (B1) to (B4). In the case where the c-Met binding nucleic acid molecule is the double-stranded nucleic acid, it may be dissociated into single strands by denaturation or the like before use, for example. Preferably, each of the single-stranded nucleic acids obtained by dissociation forms a stem structure, a loop structure, etc. as described above, for example.

The building blocks of the c-Met binding nucleic acid molecule of the present invention are not particularly limited, for example. The building blocks are nucleotide residues, for example. Examples of the nucleotide residues include ribonucleotide residues and deoxyribonucleotide residues. The c-Met binding nucleic acid molecule of the present invention may be, for example, RNA composed of only ribonucleotide residues or RNA including deoxyribonucleotide residues. In the latter case, the number of deoxyribonucleotide residues in RNA is not particularly limited, and is, for example, "one or more", which specifically is, for example, 1 to 20, preferably 1 to 10, more preferably 1 to 5, still more preferably 1 to 3, and particularly preferably 1 or 2.

The c-Met binding nucleic acid molecule of the present invention may contain a modified nucleotide residue(s), for example. The number of the modified nucleotide residues in the nucleic acid molecule is not particularly limited, and is "one or more", for example. Specifically, for example, in the polynucleotide, the number of the modified nucleotide residues is, for example, 1 to 50, preferably 1 to 40, more preferably 1 to 20, still more preferably 1 to 10, particularly preferably 1 to 3, and most preferably 1 or 2.

Examples of the modified nucleotide residue include modified ribonucleotide residues and modified deoxyribonucleotide residues. The modified nucleotide residue may be the above-described nucleotide residue with a modified sugar residue, for example. Examples of the sugar residue include ribose residues and deoxyribose residues. The modified site in the nucleotide residue is not particularly limited, and may be, for example, the 2'-position and/or the 4'-position in the sugar residue. Examples of the modification include methylation, fluorination, amination, and thiation. The modified nucleotide residue may be, for example, the one obtained by modification of a nucleotide residue having a pyrimidine base (pyrimidine nucleus) as the base, or the one obtained by modification of nucleotide residue having a purine base (purine nucleus) as the base. Among them, the former is preferable. Hereinafter, the nucleotide residue having a pyrimidine base is referred to as a "pyrimidine nucleotide residue"; a pyrimidine nucleotide residue that has been modified is referred to as a "modified pyrimidine nucleotide residue"; a nucleotide residue having a purine base is referred to as a "purine nucleotide residue"; and a purine nucleotide residue that has been modified is referred to as a "modified purine nucleotide residue". Examples of the pyrimidine nucleotide residue include: uracil nucleotide residues having uracil; cytosine nucleotide residues having cytosine; and thymine nucleotide residues having thymine. In the case where the base in the modified nucleotide residue is a pyrimidine base, for example, it is preferable that carbon in the 2'-position and/or carbon in the 4'-position in the sugar residue is modified. Specific examples of the modified nucleotide residue include modified nucleotide residues with the 2'-position in the ribose residue being modified, such as: 2'-methyluracil (2'-methylated-uracil nucleotide residue); 2'-methylcytosine (2'-methylated-cytosine nucleotide residue), 2'-fluorouracil (2'-fluorinated-uracil nucleotide residue), 2'-fluorocytosine (2'-fluorinated-cytosine nucleotide residue), 2'-aminouracil (2'-aminated-uracil nucleotide residue), 2'-aminocytosine (2'-aminated-cytosine nucleotide residue), 2'-thiouracil (2'-thiated-uracil nucleotide residue), and 2'-thiocytosine (2'-thiated-cytosine nucleotide residue).

The base in the nucleotide residue may be, for example, a natural base (a nucleic acid that is not artificial) such as adenine (a), cytosine (c), guanine (g), thymine (t), or uracil (u), or an artificial base (an unnatural base). Examples of the artificial bases include a modified base and an altered base, which both preferably has a similar function to the natural base (a, c, g, t, or u). Examples of the artificial base having the similar function include: an artificial base that can bind to cytosine (c), as a substitute for guanine (g); an artificial base that can bind to guanine (g), as a substitute for cytosine (c); an artificial base that can bind to thymine (t) or uracil (u), as a substitute for adenine (a); an artificial base that can bind to adenine (a), as a substitute for thymine (t); and an artificial base that can bind to adenine (a), as a substitute for uracil (u). Examples of the modified base include methylated bases, fluorinated bases, aminated bases, and thiated bases. Specific examples of the modified base include 2'-methyluracil, 2'-methylcytosine, 2'-fluorouracil, 2'-fluorocytosine, 2'-aminouracil, 2'-aminocytosine, 2'-thiouracil, and 2'-thiocytosine. In the present invention, for example, bases represented by a, g, c, t, and u encompass not only the natural bases but also the artificial bases having similar functions to the natural bases.

The c-Met binding nucleic acid molecule of the present invention may contain artificial nucleic acid monomer residues as the building blocks, for example. The number of the artificial nucleic acid monomer residues in the nucleic acid molecule is not particularly limited, and is, for example, "one or more", which specifically is, for example, 1 to 20, preferably 1 to 10, more preferably 1 to 5, still more preferably 1 to 3, and particularly preferably 1 or 2. Examples of the artificial nucleic acid monomer residue include PNA (peptide nucleic acid), LNA (Locked Nucleic Acid), and ENA (2'-O, 4'-C-Ethylenebridged Nucleic Acids). Bases in the above-described monomer residue are the same as described above, for example. The c-Met binding nucleic acid molecule of the present invention may be, for example, RNA or DNA containing monomer residues, which are at least any of PNA, LNA and ENA, and it preferably is RNA.

It is preferable that the c-Met binding nucleic acid molecule of the present invention is resistant to nuclease, for example. The nuclease is not particularly limited, and examples thereof include exonuclease and endonuclease. More specific examples of the nuclease include: ribonuclease (RNase), which is an enzyme that degrades RNA; deoxyribonuclease (DNase), which is an enzyme that degrades DNA; and nuclease that acts on both RNA and DNA. The method for imparting the nuclease resistance to the c-Met binding nucleic acid molecule is not particularly limited.

The c-Met binding nucleic acid molecule of the present invention preferably has the above-described modified nucleotide residue(s) as the building block(s), so that the c-Met binding nucleic acid molecule can have nuclease resistance, for example. The modified nucleotide residue is as described above, for example, and examples thereof include the above-described methylated nucleotide residue, fluorinated nucleotide residue, aminated nucleotide residue, and thiated nucleotide residue. Among them, the fluorinated nucleotide residue is preferable. The modified nucleotide residue is, for example, the pyrimidine nucleotide residue, which preferably is such that the sugar residue (ribose residue or deoxyribose residue) therein is modified. The number of the modified nucleotide residues is not particularly limited, and is as described above, for example.

The c-Met binding nucleic acid molecule of the present invention may have the above-described artificial nucleic acid monomer residue(s) as a building block(s), so that the c-Met binding nucleic acid molecule can have nuclease resistance, for example. The artificial nucleic acid monomer residue is not particularly limited, and is as described above. In particular, the LNA residue is preferable. The number of the artificial nucleic acid monomer residues is not particularly limited, and is as described above, for example.

As described above, the c-Met binding nucleic acid molecule of the present invention preferably is RNA, which preferably is resistant to ribonuclease, i.e., to RNase, for example. In this case, the c-Met binding nucleic acid molecule of the present invention preferably has the above-described deoxyribonucleotide residue(s), so that the c-Met binding nucleic acid molecule can have ribonuclease resistance, for example. Specifically, in the case where the c-Met binding nucleic acid molecule is RNA, for example, among all the nucleotide residues constituting the RNA, all or one or more of nucleotide residues having uracil may be substituted with nucleotide residues having thymin. Specifically, they may be substituted with deoxyribonucleotide residues having thymine. In the case where the c-Met binding nucleic acid molecule is RNA, for example, all or one or more of the nucleotide residues constituting the RNA may be deoxyribonucleotide residues.

The c-Met binding nucleic acid molecule of the present invention may be configured so that, for example, PEG (polyethylene glycol) or deoxythymidine is bound to its 5' end or 3' end, so that the c-Met binding nucleic acid molecule can have ribonuclease resistance. The PEG preferably is of several tens of kDa, for example.

The c-Met binding nucleic acid molecule of the present invention may further include an additional sequence (also referred to as a linker), as long as the binding property of the c-Met binding nucleic acid molecule to c-Met is not affected by the additional sequence when it is used, for example. Preferably, the additional sequence is bound to at least one of the 5' end and the 3' end of the nucleic acid molecule, more preferably to the 3' end, for example. Examples of the additional sequence include a poly (A) sequence and a poly (T) sequence. The building block of the additional sequence is a nucleotide residue, for example. Examples of the nucleotide residue include a ribonucleotide residue and a deoxyribonucleotide residue, among which the ribonucleotide residue is preferable. When the nucleic acid molecule of the present invention is immobilized on a carrier, for example, the nucleic acid molecule preferably is immobilized on the carrier via the additional sequence.

The binding activity of the c-Met binding nucleic acid molecule of the present invention to c-Met can be expressed as the dissociation constant of the c-Met binding nucleic acid molecule against c-Met, for example. The dissociation constant of the c-Met binding nucleic acid molecule of the present invention is not particularly limited, and is, for example, $5\times10^{-8}$ mol/L or less, preferably $8\times10^{-9}$ mol/L or less. The c-Met is human-derived c-Met, for example.

The c-Met binding nucleic acid molecule of the present invention not only can bind to c-Met itself, but also can bind to a fusion peptide containing c-Met via the c-Met, for example. Examples of the fusion peptide include: a fusion peptide containing c-Met on its N-terminal side; a fusion peptide containing c-Met on its C-terminal side; and a fusion peptide containing c-Met somewhere between the N terminus and the C terminus. The fusion polypeptide may contain c-Met and any other peptide, for example. The other peptide may be a protein, for example. The term "fusion peptide" also encompasses fusion proteins, for example.

The method for producing the c-Met binding nucleic acid molecule of the present invention is by no means limited, and the c-Met binding nucleic acid molecule can be synthesized by known methods such as nucleic acid synthesis utilizing chemical synthesis.

The c-Met binding nucleic acid molecule of the present invention also can be prepared by nucleic acid amplification, for example. The method for preparing the c-Met binding nucleic acid molecule by the nucleic acid amplification is not particularly limited. In the case where the c-Met binding nucleic acid molecule of the present invention is RNA, it can be prepared using DNA as a template, for example. Hereinafter, the DNA strand serving as the template for the RNA also is referred to as an antisense strand, and the DNA strand including a sequence obtained by substitution of uracil (u) with thymine (t) in the RNA also is referred to as a sense strand. The template DNA preferably includes, for example, at least one of DNA obtained by substitution of uracil (u) with thymine (t) in the complementary strand of the X region in the RNA (antisense strand), and DNA including a sequence obtained by substitution of uracil (u) with thymine (t) in the X region (sense strand). Nucleic acid amplification is carried out using DNA-dependent DNA polymerase with the above-described DNA as a template. Thereafter, with the thus-obtained DNA amplification product as a template, RNA is transcribed using DNA-dependent RNA polymerase. In this manner, the RNA can be amplified. Alternatively, with the RNA as a template, cDNA is prepared through a reverse transcription reaction using RNA-dependent DNA polymerase. Thereafter, with the thus-obtained cDNA as a template, nucleic acid amplification of DNA is carried out by PCR or the like. Then, with the thus-obtained DNA amplification product as a template, RNA is transcribed using DNA-dependent RNA polymerase. The RNA also may be amplified in this manner.

In the case where the c-Met binding nucleic acid molecule of the present invention is DNA, the DNA can be amplified by the polymerase chain reaction (PCR) method or the like, for example.

Since the c-Met binding nucleic acid molecule of the present invention can bind to c-Met, it can be used as a neutralizer that neutralizes the function of c-Met by binding to c-Met, for example.

Since the c-Met binding nucleic acid molecule of the present invention can bind to c-Met as described above, it can be used as an inhibitor that inhibits the function of c-Met by binding to c-Met, for example.

Since the c-Met binding nucleic acid molecule of the present invention can bind to c-Met, it can be used as a pharmaceutical agent for preventing or treating diseases caused by the expression of c-Met, for example. Examples of the diseases include: cancers, hepatopathy, amyotrophic lateral sclerosis, and infectious inflammation. Examples of the hepatopathy include chronic hepatitis, fatty liver, and liver cirrhosis. Examples of the infectious inflammation include bacterial infection and Plasmodium infection. The pharmaceutical agent of the present invention can be used as an anticancer agent, an antihepatopathy agent, an anti-amyotrophic lateral sclerosis agent, an antiinflammatory agent, or the like, for example.

The neutralizer of the present invention, the inhibitor of the present invention, and the pharmaceutical agent of the present invention are by no means limited as long as they contain the c-Met binding nucleic acid molecule of the present invention. The neutralizer of the present invention, the inhibitor of the present invention, and the pharmaceutical agent of the present invention may each contain not only the c-Met binding nucleic acid molecule of the present invention but also a carrier or the like, for example. They may have the same configuration as a composition to be described below, and they can be used in the same way as the composition, for example.

The c-Met binding nucleic acid molecule of the present invention can inhibit, for example, cell movement (migration) and/or cell infiltration, which is, for example, cell movement and/or cell infiltration promoted by HGF. The c-Met binding nucleic acid molecule of the present invention also can be used as an inhibitor for cell movement, an inhibitor for cell migration, or an inhibitor for cell infiltration. Moreover, since the c-Met binding nucleic acid molecule of the present invention can inhibit the movement or the like of cells, it can be used as an inhibitor for cancer metastasis, for example.

<Composition>

The composition of the present invention is characterized in that it contains the c-Met binding nucleic acid molecule of the present invention, as described above. The composition of the present invention is by no means limited, as long as it contains the c-Met binding nucleic acid molecule of the present invention.

Since the composition of the present invention can bind to c-Met as described above, it can be used as a neutralizer that neutralizes the function of c-Met by binding to c-Met, for example.

Since the composition of the present invention can bind to c-Met as described above, it can be used as an inhibitor that inhibits the function of c-Met by binding to c-Met, for example.

Since the composition of the present invention can bind to c-Met as described above, it can be used as a pharmaceutical agent for preventing or treating diseases caused by c-Met, for example. The pharmaceutical agent of the present invention can be used as an anticancer agent or the like, for example.

A subject to which the composition of the present invention is applied is not particularly limited, and can be determined as appropriate depending on the use of the composition. The subject may be, for example, a cell, a tissue, a living organism, or the like. The origin of the cell or the tissue, and the kind of the living organism is not particularly limited. Examples of the living organism include living things that have a c-Met gene and/or a c-Met ortholog gene, and specific examples thereof include: humans; nonhuman mammals, i.e., mammals excluding humans; and animals such as birds and fishes. In the case where the composition of the present invention is administered to a living organism, the administration method is not particularly limited, and examples thereof include oral administration and parenteral administration. Examples of the parenteral administration include: intravenous administration; intraarterial administration; administration to a lymphatic vessel; intramuscular administration; subcutaneous administration; rectal administration; transdermal administration; intraperitoneal administration; and local administration.

The composition of the present invention may contain various kinds of additives, in addition to the c-Met binding nucleic acid molecule of the present invention, for example. The additives are not particularly limited, and can be determined as appropriate depending on the use of the composition of the present invention, for example. It is preferable that the additives are pharmaceutically acceptable, for example.

In the case where the composition of the present invention is used for delivering the c-Met binding nucleic acid molecule to a cell, a tissue, a living organism, or the like, for example, it is preferable that the composition further contains a carrier as the additive. The carrier is not particularly limited, and examples thereof include nano-particles, liposome, micelles, reversed micelles, polycations, cell-penetrating peptides, magnetic particles, and calcium phosphate. The nano-particles are not particularly limited, and examples thereof include nanocarbons such as carbon nanohorns and carbon nanotubes. One of these carriers may be used alone, or two or more of them may be used in combination. Further examples of the additive include buffers, metal salts, and surfactants.

<Detection Reagent and Kit>

The detection reagent of the present invention is a c-Met detection reagent for detecting c-Met, which is characterized in that it contains the c-Met binding nucleic acid molecule of the present invention. The detection reagent of the present invention is by no means limited, as long as it contains the c-Met binding nucleic acid molecule of the present invention.

The c-Met binding nucleic acid molecule of the present invention can bind to c-Met, as described above. Thus, for example, it is possible to detect c-Met in a sample by checking the presence or absence of the binding between the c-Met binding nucleic acid molecule of the present invention and the c-Met using the detection reagent of the present invention. As the detection, both qualitative detection and quantitative detection are possible, for example. The method for checking the presence or absence of the binding between the c-Met binding nucleic acid molecule and the c-Met is not particularly limited, and it is possible to use a known method for detecting the binding between nucleic acid and a protein. As described above, c-Met can be detected easily by using the detection reagent of the present invention. Thus, the detection reagent of the present invention is useful in the field of biochemistry and in clinical practice, for example.

The kit of the present invention is characterized in that it includes the c-Met binding nucleic acid molecule of the present invention. According to the kit of the present invention, it is possible to detect c-Met as described above, for example.

The kit of the present invention may include, for example, various kinds of additives, an instructions for use, and the like, as necessary.

<Treatment Method>

The treatment method according to the present invention includes the step of administering the c-Met binding nucleic acid molecule of the present invention to a subject having a disease in which c-Met is involved. The disease in which c-Met is involved is not particularly limited, and it may be at least one disease selected from the group consisting of cancers, hepatopathy, amyotrophic lateral sclerosis, and infectious inflammation, for example. Examples of the cancers include cancers in the liver, kidney, pancreas, lung, bladder, prostate, seminal vesicle, ovary, breast, mammary gland, and digestive tracts such as the stomach and colon. Examples of the hepatopathy include chronic hepatitis, fatty liver, and liver cirrhosis. Examples of the infectious inflammation include bacterial infection and Plasmodium infection. According to the treatment method of the present invention, prevention of the disease, inhibition of the progress of the disease, treatment of the disease, and the like are possible, for example. The treatment method of the present invention also encompasses a prevention method, for example, and may include the step of administering the c-Met binding nucleic acid molecule of the present invention to a subject with the risk of the disease. The administration method of the c-Met binding nucleic acid molecule of the present invention, the administration conditions, etc. are not particularly limited, and are as described above. Also, a subject to which the c-Met binding nucleic acid molecule of the present invention is administered (e.g., a patient) is not particularly limited. Examples of the living organism include living things that have a c-Met gene and/or a c-Met ortholog gene, and specific examples thereof include: humans and nonhuman animals, i.e., animals excluding humans. Examples of the nonhuman animals include: nonhuman mammals, i.e., mammals excluding humans; birds; and fishes. In the administration step, the composition of the present invention may be administered, for example.

The present invention provides a nucleic acid molecule for use in the treatment of a diseases in which c-Met is involved. The nucleic acid molecule is the c-Met binding nucleic acid molecule of the present invention. The c-Met binding nucleic acid molecule of the present invention is as described above. The present invention also provides a composition for use in the treatment of a disease in which c-Met is involved. The composition is the composition of the present invention, which contains the c-Met binding nucleic acid molecule of the present invention. The composition of the present invention is as described above.

The method for inhibiting cell movement according to the present invention includes the step of administering the c-Met binding nucleic acid molecule of the present invention to cells. Unless otherwise stated, the above description can be referred to, for example. The administration may be carried out either in vivo or in vitro, for example. The kind of the cells is by no means limited, and examples thereof include: cells with the above-described cancers; cells cultured therefrom; and cells isolated from a patient. The method for inhibiting cell movement according to the present invention also can be referred to as a method for inhibiting cell migration or a method for inhibiting cell infiltration, for example. Moreover, since the c-Met binding nucleic acid molecule of the present invention can inhibit the movement or the like of cells, for example, the method for inhibiting cell movement according to the present invention also can be referred to as a method for inhibiting cancer metastasis, for example.

EXAMPLES

Next, the present invention will be described with reference to examples. It is to be noted, however, that the present invention is by no means limited by the following examples. Unless otherwise stated, commercially available reagents in the following examples were used in accordance with their protocols.

Example 1

RNA aptamers capable of binding to c-Met were produced as c-Met binding nucleic acid molecules, and the binding ability of each of the RNA aptamers to c-Met was examined.

(1) RNA Aptamers

RNA aptamers consisting of the base sequences of SEQ ID NOs: 39 to 48 shown in Table 2 below were produced by a known nucleic acid synthesis method. These RNA aptamers were used as RNA aptamers of Example 1. As RNAs of Comparative Example 1, an RNA library (40N) was used, which contained a plurality of RNAs each consisting of an oligonucleotide of the following SEQ ID NO: 90 with a 40-mer random sequence (the same applies hereinafter). In SEQ ID NO: 90, "n" indicates adenine, guanine, cytosine, thymine, or uracil.

40N (SEQ ID NO: 90)

gggacgcucacguacgcucannnnnnnnnnnnnnnnnnnnnnnnnnnnnnnnnnnnnnnnucagugccuggacgugcagu

TABLE 2

| Aptamer | Sequence | SEQ No. |
|---|---|---|
| g1 | GGGACGCUCACGUACGCUAA ACACACUGAGAGUUUGACCAGCUAUUAAAUGGGUCGUGAC UCAGUGCCUGGACGUGCAGU | 39 |
| g2 | GGGACGCUCACGUACGCUAA ACCCUGGCGAUCUCCGGCCGGAUACGGGAGAACGAGGUAC UCAGUGCCUGGACGUGCAGU | 40 |
| g3 | GGGACGCUCACGUACGCUAA GGGCGAAACUGUCGUGACACGGUUUGACAUGCCGGCCUUA UCAGUGCCUGGACGUGCAGU | 41 |
| g4 | GGGACGCUCACGUACGCUAA UACCGUGAUUCGGGGUGGUAUCCGGUGGACAUCCAGGUCG UCAGUGCCUGGACGUGCAGU | 42 |
| g5 | GGGACGCUCACGUACGCUAA GCCCAACGAACAUUUUGAGUUUCCAGGCAGCUCAUAGACA UCAGUGCCUGGACGUGCAGU | 43 |
| g6 | GGGACGCUCACGUACGCUAA UCCAGGUGUGGCGAGCCACUGUAAGAGUCGCCGUGAGGAU UCAGUGCCUGGACGUGCAGU | 45 |
| g7 | GGGACGCUCACGUACGCUAA CUUGAAGUCAAGGGUAGAGUGACCAUGCAGCUCGUAGACA UCAGUGCCUGGACGUGCAGU | 46 |
| g8 | GGGACGCUCACGUACGCUAA GGGCACUUAAAACCAGACCGUGAUUUGCGGUUGGUCUCGC UCAGUGCCUGGACGUGCAGU | 47 |
| g9 | GGGACGCUCACGUACGCUAA GAUGUCUCAAUUGGUCGUGAUUGUGCUGACCACACGAACC UCAGUGCCUGGACGUGCAGU | 48 |

(2) Target Protein

Figures 2, 3:
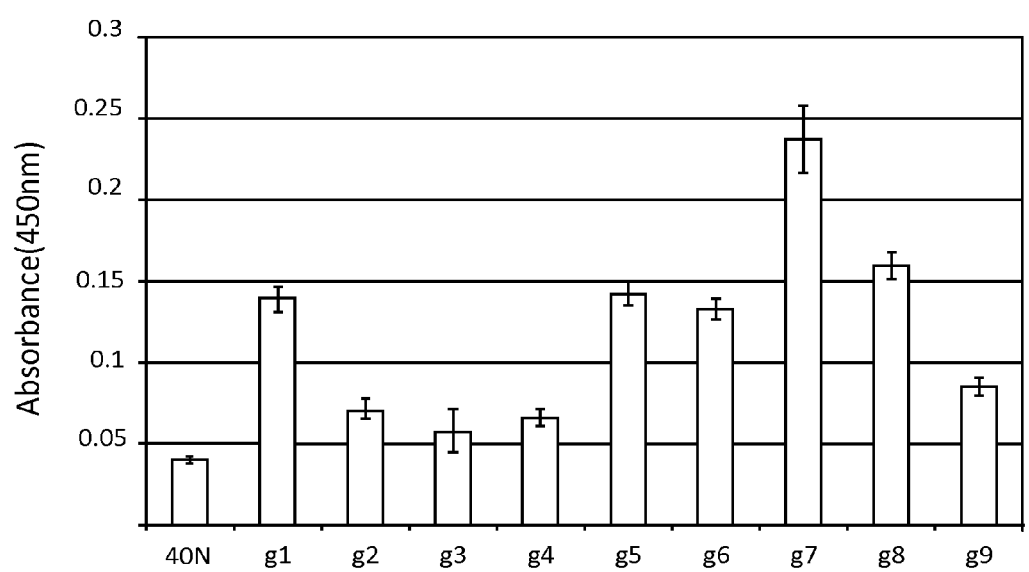
FIG. 2 is a schematic view showing a diagrammatic illustration of a recombinant c-Met.
FIG. 3 is a graph showing the binding ability of each RNA aptamer to the recombinant c-Met in Example 1 of the present invention.

As a target protein, a recombinant protein including a His-tag, IgG, and c-Met was used. As the recombinant protein, a commercially available product with the trade name "Recombinant Human HGF R/c-MET/Fc Chimera, CF" (R & D Systems) was used (this recombinant protein hereinafter is referred to as "rec-cMet"). FIG. 2 schematically shows the structure of the rec-cMet. In FIG. 2, the left side of the rec-cMet is the N terminus, and the right side of the same is the C terminus. "cMet α" is a peptide sequence (SEQ ID NO: 91) from the 25th Glu to the 307th Arg in the α chain of c-Met (NCBI Accession No. P08581). "cMet β" is a peptide sequence (SEQ ID NO: 92) from the 308th Ser to the 932nd Thr in the β chain of c-Met (NCBI Accession No. P08581). "HIEGRMD" is a peptide sequence (SEQ ID NO: 93) consisting of seven amino acid residues His-Ile-Glu-Gly-Arg-Met-Asp. "IgG" is a peptide sequence (SEQ ID NO: 94) from the 100th Pro to 330th Lys in human IgG. "6 His" is a His-tag (SEQ ID NO: 95) consisting of six His residues linked together. In the rec-cMet, the cMet α and the cMet β are bound together by disulfide bonds, and to the C terminus of the cMet β, the HIEGRMD, the IgG, and the His-tag are linked in this order.

(3) Improved ELISA Method

An anti-IgG antibody (trade name: "Human IgG-Fc Antibody", Bethyl Laboratories) was adsorbed on a 96-well plate (Iwaki, AGC Techno Glass Co., Ltd., Japan), and then was subjected to blocking using 1% bovine serum albumin. Subsequently, 50 μL of the 1 μg/mL rec-cMet was added to the plate. Further, Tris (20 mmol/L), sodium chloride (100 mmol/L), magnesium acetate (0.1 mmol/L) and Triton (registered trademark)-X100 (0.2%) were added to the plate so that their final concentrations would be as shown in the parentheses. The plate was incubated at room temperature for 3 hours, thus causing the rec-cMet to bind to the plate. After the incubation, the plate was washed three times with a washing solution. The composition of the washing solution was as follows: 20 mmol/L Tris, 100 mmol/L sodium chloride, 0.1 mmol/L magnesium acetate, and 0.2% Triton (registered trademark)-X100. As a control, incubation and washing were carried out in the same manner, except that 50 μL of the washing solution was added instead of 50 μL of the rec-cMet.

Next, a 20-mer polyadenine (poly A) was added to the 3' end of each of the RNA aptamers. Thus, poly-A-added RNA aptamers were prepared. Each of the poly-A-added RNA aptamers was denatured, and thereafter, the denatured poly-A-added RNA aptamer was mixed with a 20-mer biotinylated polythymine with its 5' end being biotinylated (740 nmol/L), tRNA (100 μg/mL), and an RNase inhibitor (0.16 units/mL). As a result, complementary binding occurred between the poly A in the poly-A-added RNA aptamer and the polythymine (poly T) in the biotinylated polythymine, whereby a biotin-labeled RNA aptamer was produced. The biotin-labeled RNA aptamer was added to the plate, and the plate was incubated at 4° C. for 30 minutes. Subsequently, the plate was washed, and 0.1 μg/mL HRP-streptavidin (Thermo Fisher Scientific Inc., USA) was added thereto. The plate was then washed, after which a 1-Step Ultra TMB substrate (Thermo Fisher Scientific Inc., USA) was added to the plate to cause color development, and the absorbance at 450 nm was measured.

The results thereof are shown in FIG. 3. FIG. 3 is a graph showing the binding ability of each of the RNA aptamers g1 to g9 to the rec-cMet. In FIG. 3, the vertical axis indicates the absorbance at 450 nm, which indicates the binding ability to the rec-cMet. The absorbance shown in the graph is the mean value±deviation (SD), determined based on three times measurement. In FIG. 3, the respective bars indicate, from the left, the results obtained regarding the 40N and the RNA aptamers g1 to g9.

As shown in FIG. 3, the RNA aptamers g1 to g9 all exhibited a higher absorbance than the 40N. From these results, it can be seen that the RNA aptamers g1 to g9 bind to the rec-cMet. Among these RNA aptamers, the RNA aptamers g1, g5, g6, g7, and g8 exhibited a high binding ability, and in particular, the RNA aptamer g7 exhibited an excellent binding ability.

Example 2

Regarding all the RNA aptamers of Example 1, it was examined whether or not the binding thereof to the rec-cMet is specific binding to the c-Met region in the rec-cMet.

As a target protein, a recombinant protein (6 His) was used, which includes the following sequences linked together from the N-terminal side: a peptide sequence of an NGFR protein (SEQ ID NO: 96), a peptide sequence consisting of seven amino acid residues (DIEGRMD: SEQ ID NO: 97), a peptide sequence of human IgG (SEQ ID NO: 94), and His-tag (SEQ ID NO: 95). As the recombinant protein, a commercially available product with the trade name "Recombinant Human NGF R/TNFRSF16/Fc Chimera, CF" (R & D Systems) was used (this recombinant protein hereinafter is referred to as "rec-NGFR"). In the rec-NGFR, the peptide sequence of the NGFR protein is a peptide sequence (SEQ ID NO: 96) from the 29th Lys to the 250th Asn in the NGFR protein (NCBI Accession No. P08138). The peptide sequence consisting of seven amino acid residues is a peptide sequence (SEQ ID NO: 97) consisting of seven amino acid residues Asp-Ile-Glu-Gly-Arg-Met-Asp. The peptide sequence of human IgG is a peptide sequence (SEQ ID NO: 94) from the 100th Pro to the 330th Lys in the human IgG. The His-tag is a peptide sequence consisting of six His residues linked together.

The binding ability of each of the RNA aptamers to the rec-NGFR was examined in the same manner as in Example 1, except that the rec-NGFR was bound to the plate. Also, as a comparative example, the 40N was used, and the binding ability thereof was examined in the same manner.

Figure 4:
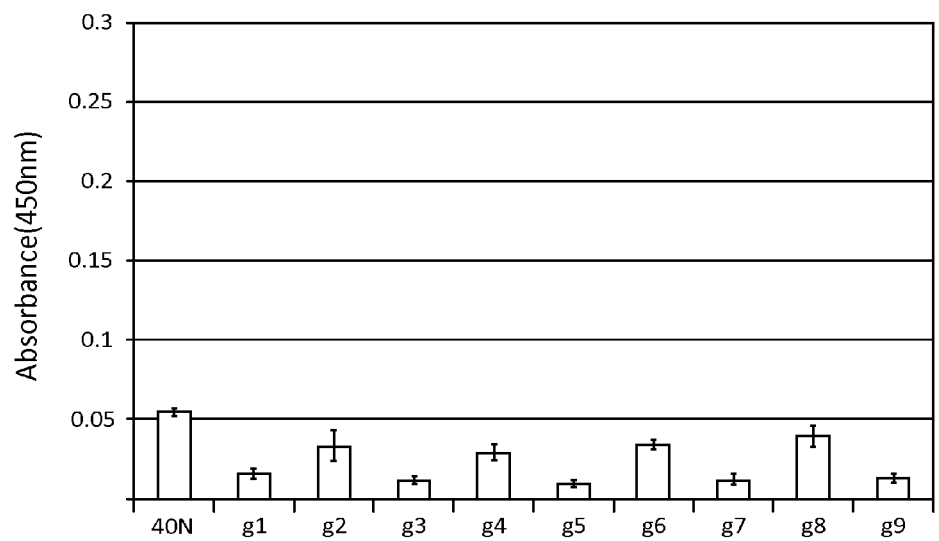
FIG. 4 is a graph showing the binding ability of each RNA aptamer to a recombinant NGFR in Example 2 of the present invention.

The results thereof are shown in FIG. 4. FIG. 4 is a graph showing the binding ability of each of the RNA aptamers g1 to g9 to the rec-NGFR. In FIG. 4, the vertical axis indicates the absorbance at 450 nm, which indicates the binding ability to the rec-NGFR. The absorbance shown in the graph is the mean value±deviation (SD), determined based on three times measurement. In FIG. 4, the respective bars indicate, from the left, the results obtained regarding the 40N and the RNA aptamers g1 to g9.

As shown in FIG. 4, the RNA aptamers g1 to g9 all exhibited a lower absorbance than the 40N, from which it was found that the RNA aptamers g1 to g9 were not bound to the rec-NGFR. These results demonstrate that, in Example 1, each of the RNA aptamers was specifically bound to the c-Met region in the rec-cMet.

Figure 5:
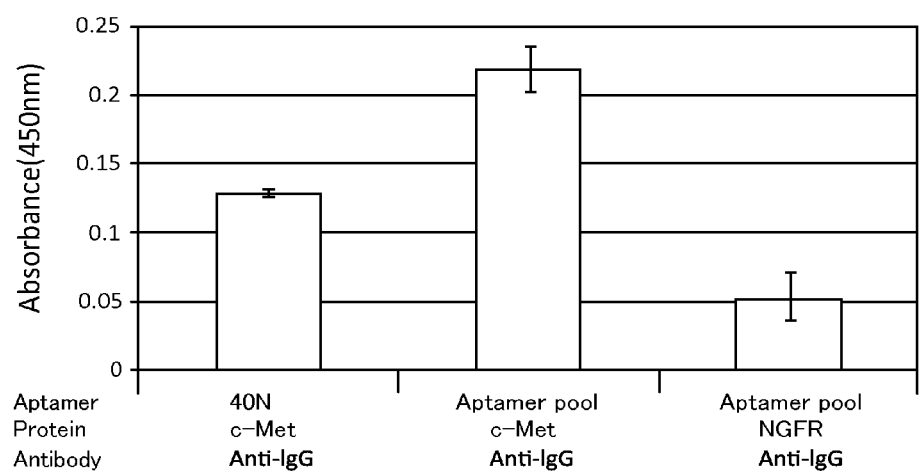
FIG. 5 is a graph showing the binding ability of an RNA aptamer pool to the recombinant c-Met in Example 2 of the present invention.

Also, regarding an aptamer pool containing the RNA aptamers g1 to g9, FIG. 5 shows the binding ability thereof to the rec-cMet and to the rec-NGFR. FIG. 5 is a graph showing the binding ability of the aptamer pool to the rec-cMet and the rec-NGFR. In FIG. 5, the vertical axis indicates the absorbance at 450 nm, which indicates the binding ability to each of the recombinant proteins. The absorbance shown in the graph is the mean value±deviation (SD), determined based on three times measurement. In FIG. 5, the respective bars indicate, from the left, the results regarding: the binding ability of the 40N to the rec-cMet; the binding ability of the aptamer pool to the rec-cMet; and the binding ability of the aptamer pool to the rec-NGFR.

As can be seen from FIG. 5, the RNA aptamer pool exhibited a higher absorbance than the 40N when the target protein was the rec-cMet, whereas it exhibited a very low absorbance when the target protein was the rec-NGFR. These results demonstrate that the RNA aptamer pool binds specifically to c-Met, not to NGFR.

Example 3

Aptamers were produced by truncating the RNA aptamer g1 (SEQ ID NO: 39), and the binding ability of each of the truncated aptamers to c-Met was examined.

(1) RNA Aptamers

FIG. 1 shows a schematic view of the predicted secondary structure of the RNA aptamer g1. As the truncated RNA aptamers, the following aptamers were produced: g1-u5del obtained by deletion of the 4th to 8th bases (5-mer) on the 5' side of the sequence of the RNA aptamer g1; g1-u10del obtained by deletion of the 4th to 13th bases (10-mer) on the 5' side of the same; g1-d5del obtained by deletion of the 1st to 5th bases (5-mer) from the 3' end of the sequence of the RNA aptamer g1; and g1-d10del obtained by deletion of the 1st to 10th bases (10-mer) from the 3' end of the same. The sequences of these truncated aptamers are shown in Table 3 below.

TABLE 3

| Aptamer | Sequence | SEQ No. |
|---|---|---|
| g1 | GGGACGCUCACGUACGCUAA ACACACUGAGAGUUUGACCAGCUAUUAAAUGGGUCGUGAC UCAGUGCCUGGACGUGCAGU | 39 |
| g1-u5del | GGG CACGUACGCUAA ACACACUGAGAGUUUGACCAGCUAUUAAAUGGGUCGUGAC UCAGUGCCUGGACGUGCAG | 81 |
| g1-u10del | GGG ACGCUAA ACACACUGAGAGUUUGACCAGCUAUUAAAUGGGUCGUGAC UCAGUGCCUGGACGUGC | 82 |
| g1-d5del | GGGACGCUCACGUACGCUAA ACACACUGAGAGUUUGACCAGCUAUUAAAUGGGUCGUGAC UCAGUGCCUGGACGU | 84 |
| g1-d10del | GGGACGCUCACGUACGCUAA ACACACUGAGAGUUUGACCAGCUAUUAAAUGGGUCGUGAC UCAGUGCCUG | 85 |

The binding ability of each of the RNA aptamers to the rec-cMet was examined in the same manner as in Example 1, except that the truncated RNA aptamers were used. Also, the binding ability of the RNA aptamer g1 was examined in the same manner. As a comparative example, the 40N was used, and the binding ability thereof was examined in the same manner.

Figure 6:
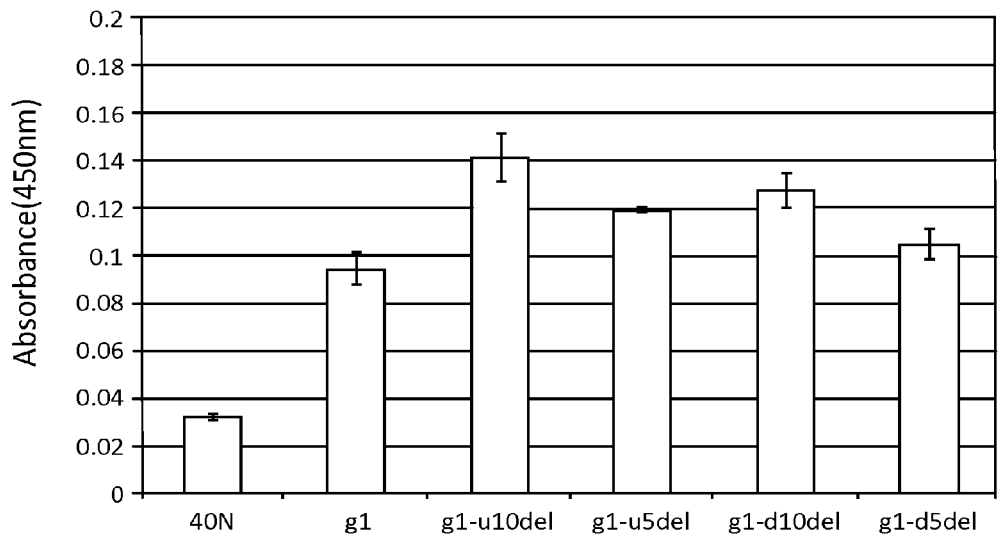
FIG. 6 is a graph showing the binding ability of each RNA aptamer to the recombinant c-Met in Example 3 of the present invention.

The results thereof are shown in FIG. 6. FIG. 6 is a graph showing the binding ability of each of the truncated aptamers g1-u10del, g1-u5del, g1-d5del, and g1-d10del to the rec-cMet. In FIG. 6, the vertical axis indicates the absorbance at 450 nm, which indicates the binding ability to the rec-cMet. The absorbance shown in the graph is the mean value±deviation (SD), determined based on three times measurement. In FIG. 6, the respective bars indicate, from the left, the results obtained regarding the 40N, the RNA aptamer g1, and the truncated RNA aptamers g1-u10del, g1-u5del, g1-d10del, and g1-d5del.

As shown in FIG. 6, the truncated RNA aptamers g1-u10del, g1-u5del, g1-d10del, g1-d5del all exhibited a higher absorbance than the RNA aptamer g1. From these results, it was found that the binding ability of the RNA aptamer g1 to c-Met is improved by truncating the RNA aptamer g1.

Example 4

Aptamers were produced by truncating the RNA aptamer g1 (SEQ ID NO: 39), and the binding ability of each of the truncated aptamers to c-Met was examined.

(1) RNA Aptamers

Figure 7:
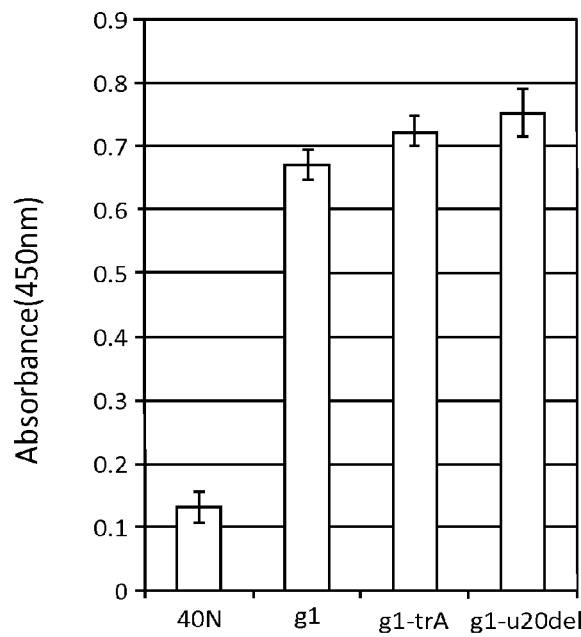
FIG. 7 is a graph showing the binding ability of each RNA aptamer to the recombinant c-Met in Example 4 of the present invention.

FIG. 1 shows a schematic view of the predicted secondary structure of the RNA aptamer g1. As the truncated RNA aptamers, the following aptamers were produced: g1-u20del obtained by deletion of the 4th to 23rd bases (20-mer) on the 5' side of the sequence of the RNA aptamer g1; and g1-trA obtained by deletion of the 4th to 23 bases (20-mer) on the 5' side and the 1st to 14th bases (14-mer) on the 3' side of the sequence of the RNA aptamer g1. The sequences of these truncated aptamers are shown in Table 4 below.

three times measurement. In FIG. 7, the respective bars indicate, from the left, the results obtained regarding the 40N, the RNA aptamer g1, and the truncated RNA aptamers g1-trA and g1-u20del.

As can be seen from FIG. 7, the truncated RNA aptamers g1-trA and g1-u20del each exhibited a higher absorbance than the RNA aptamer g1. From these results, it was found that the binding ability of the RNA aptamer g1 to c-Met is improved by truncating the RNA aptamer g1.

Example 5

Aptamers were produced by further truncating the RNA aptamer g1-trA (SEQ ID NO: 86), and the binding ability of each of the thus-produced truncated aptamers to c-Met was examined.

(1) RNA Aptamers

Figure 8:
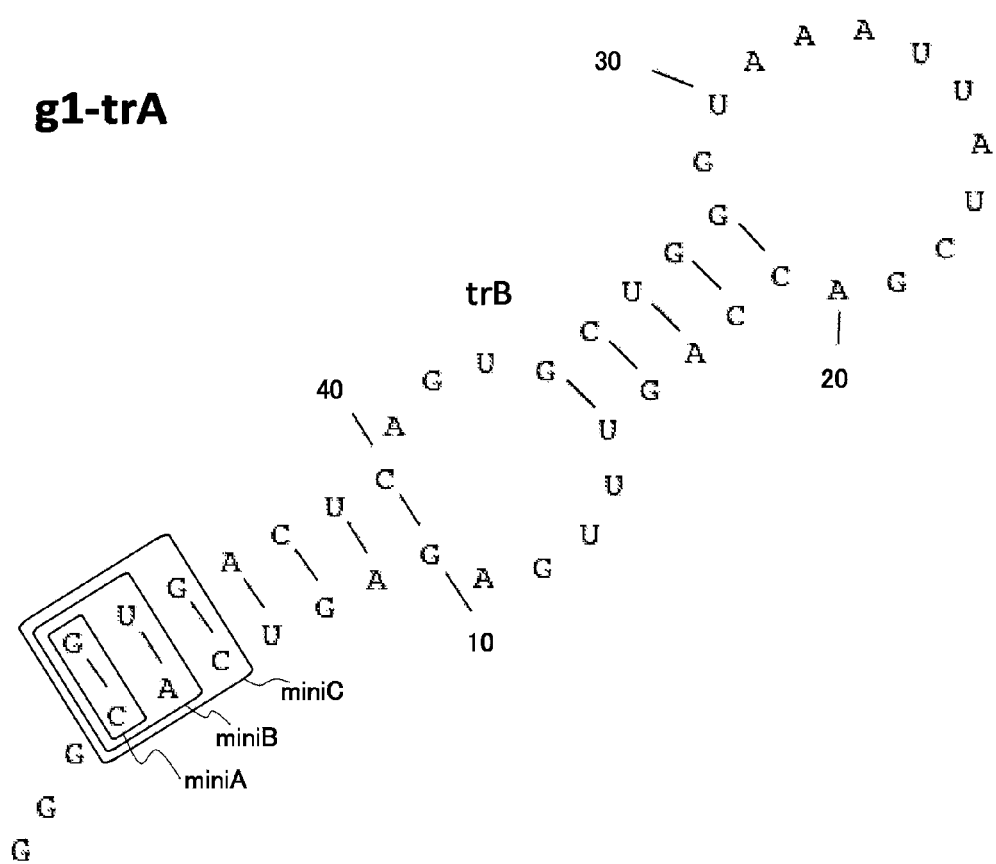
FIG. 8 is a schematic view showing the predicted secondary structure of an RNA aptamer g1-trA (SEQ ID NO: 86) in the present invention.

FIG. 8 shows a schematic view of the predicted secondary structure of the RNA aptamer g1-trA. As the truncated RNA aptamers, the following aptamers were produced: g1-miniA obtained by deletion of the 4th base on the 5' side and the 1st base at the 3' end in the sequence of the RNA aptamer g1-trA; g1-miniB obtained by deletion of the 4th to 5th bases (2-mer) on the 5' side and the 1st to 2nd bases (2-mer) on the 3' side of the same; and g1-miniC obtained by deletion of the 4th to 6th bases (3-mer) on the 5' side and the 1st to 3rd bases (3-mer) on

TABLE 4

| Aptamer | Sequence | SEQ No. |
|---|---|---|
| g1 | GGGACGCUCACGUACGCUAA ACACACUGAGAGUUUGACCAGCUAUUAAAUGGGUCGUGAC UCAGUGCCUGGACGUGCAGU | 39 |
| g1-u20del | GGG CACUGAGAGUUUGACCAGCUAUUAAAUGGGUCGUGAC UCAGUGCCUGGACGUG | 83 |
| g1-trA | GGG CACUGAGAGUUUGACCAGCUAUUAAAUGGGUCGUGAC UCAGUG | 86 |

The binding ability of each of the RNA aptamers to the rec-cMet was examined in the same manner as in Example 1, except that the truncated RNA aptamers were used. Also, the binding ability of the RNA aptamer g1 was examined in the same manner. As a comparative example, the 40N was used, and the binding ability thereof was examined in the same manner.

The results thereof are shown in FIG. 7. FIG. 7 is a graph showing the binding ability of each of the truncated aptamers g1-trA and g1-u20del to the rec-cMet. In FIG. 7, the vertical axis indicates the absorbance at 450 nm, which indicates the binding ability to the rec-cMet. The absorbance shown in the graph is the mean value±deviation (SD), determined based on the 3' side of the same. As shown in FIG. 8, the RNA aptamer g1-miniA was obtained by deletion of one base pair from the stem region of the RNA aptamer g1-trA, the RNA aptamer g1-miniB was obtained by deletion of two base pairs from the stem region of the same, and the RNA aptamer g1-miniC was obtained by deletion of three base pairs from the stem region of the same. The base sequences of these truncated aptamers are shown in Table 5 below.

TABLE 5

| Aptamer | Sequence | SEQ No. |
|---|---|---|
| g1-trA | GGG CACUGAGAGUUUGACCAGCUAUUAAAUGGGUCGUGAC UCAGUG | 86 |
| g1-miniA | GGG ACUGAGAGUUUGACCAGCUAUUAAAUGGGUCGUGAC UCAGU | 87 |
| g1-miniB | GGG CUGAGAGUUUGACCAGCUAUUAAAUGGGUCGUGAC UCAG | 88 |
| g1-miniC | GGG UGAGAGUUUGACCAGCUAUUAAAUGGGUCGUGAC UCA | 89 |

Using these truncated RNA aptamers, the binding ability thereof to the rec-cMet was examined. The binding ability was analyzed using BIACORE (registered trademark) X (GE Healthcare) in accordance with its instructions for use, with the concentration of the rec-cMet being set to 175 nmol/L. Also, the binding ability of each of the RNA aptamers g1 and g1-trA was examined in the same manner. As a comparative example, the 40N was used, and the binding ability thereof was examined in the same manner.

Figure 9:
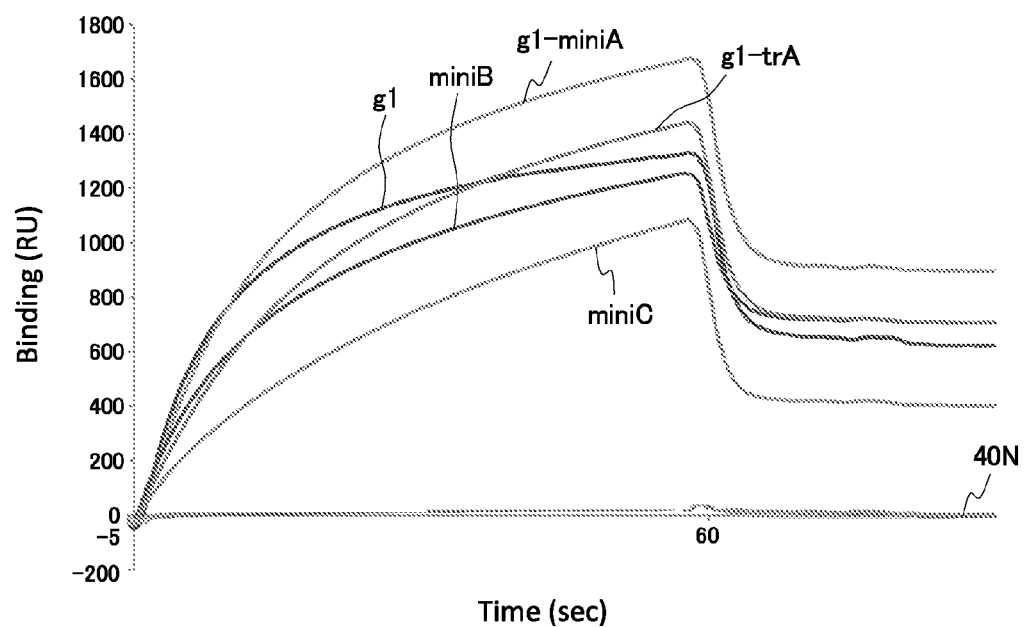
FIG. 9 is a graph showing the binding ability of each RNA aptamer to the recombinant c-Met in Example 5 of the present invention.

The results thereof are shown in FIG. 9. FIG. 9 is a graph showing the binding ability of each of the truncated aptamers to the rec-cMet. In FIG. 9, the vertical axis indicates the signal intensity (RU) measured with the BIACORE (registered trademark) X, and the horizontal axis indicates the analysis time (seconds).

As shown in FIG. 9, the truncated RNAs each exhibited the binding ability to the rec-cMet. In particular, g1-miniA exhibited a high binding ability. The dissociation constants (KD) of g1-trA, g1-miniA, and g1-miniB were as follows: g1-trA: $8.18 \times 10^{-9}$ mol/L, g1-miniA: $7.98 \times 10^{-9}$ mol/L, and g1-miniB: $2.64 \times 10^{-8}$ mol/L. From these results, it was found that they each have a high binding ability.

Example 6

RNA aptamers shown below were produced, and the binding ability of each of the RNA aptamers to c-Met was examined.

(1) RNA aptamers g1 (#6: SEQ ID NO: 39), g28 (#56: SEQ ID NO: 66), g6 (#18: SEQ ID NO: 44), g21 (#25: SEQ ID NO: 59), g34 (#73: SEQ ID NO: 72), g37 (#71: SEQ ID NO: 75), g5 (#20: SEQ ID NO: 43), g7 (#32: SEQ ID NO: 45), g25 (#51: SEQ ID NO: 63) g2 (#28: SEQ ID NO: 40), g33 (#64: SEQ ID NO: 71), g27 (#43: SEQ ID NO: 65), g20 (#35: SEQ ID NO: 58), g11 (#21: SEQ ID NO: 49), g35 (#63: SEQ ID NO: 73), g23 (#44: SEQ ID NO: 61), g15 (#39: SEQ ID NO: 53), g14 (#23: SEQ ID NO: 52), g17 (#26: SEQ ID NO: 55), g13 (#14: SEQ ID NO: 51)
g4 (#16: SEQ ID NO: 42), g31 (#95: SEQ ID NO: 69), g29 (#49: SEQ ID NO: 67), g19 (#27: SEQ ID NO: 57), g9 (#8: SEQ ID NO: 47), g10 (#1: SEQ ID NO: 48), g8 (#33: SEQ ID NO: 46), g32 (#88: SEQ ID NO: 70), g30 (#70: SEQ ID NO: 68)
g3 (#47: SEQ ID NO: 41), g16 (#24: SEQ ID NO: 54), g26 (#65: SEQ ID NO: 64), g36 (#87: SEQ ID NO: 74), g38 (#50: SEQ ID NO: 76), g18 (#17: SEQ ID NO: 56), g22 (#30: SEQ ID NO: 60), g12 (#36: SEQ ID NO: 50), g24 (#89: SEQ ID NO: 62)

The binding ability of each of the RNA aptamers to the rec-cMet was examined in the same manner as in Example 5, except that the above RNA aptamers were used. The concentration of the rec-cMet was set to 100 nmol/L. With the time point at which the introduction of the rec-cMet to the chip was started being 0 seconds, introduction of a buffer was started 60 seconds later. As a comparative example, RNA that does not specifically bind to the rec-cMet was used as a negative control, and the binding ability of this negative control was examined in the same manner.

Figure 11:
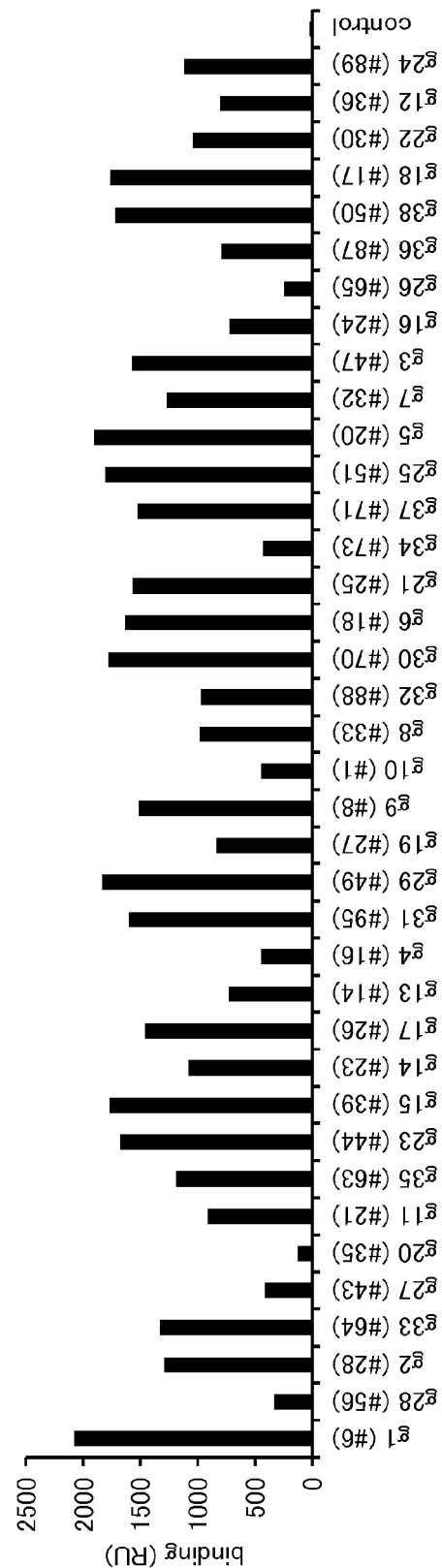
FIG. 11 is a graph showing the binding ability of each RNA aptamer to the recombinant c-Met in Example 6 of the present invention.

The results thereof are shown in FIG. 11. FIG. 11 is a graph showing the binding ability of each of the RNA aptamers to the rec-cMet. In FIG. 11, the vertical axis indicates the signal intensity (RU) measured with the BIACORE (registered trademark) X. The signal intensity shown in the graph is a value measured at the 60th second when the buffer was introduced. As shown in FIG. 11, the RNA aptamers all exhibited a binding force. All the RNA aptamers maintained equivalent signal values subsequent to the 60th second. Thus, it was confirmed that no decrease in binding ability occurred.

Example 7

Modified RNA aptamers shown below were produced, and the binding ability of each of the RNA aptamers to c-Met was examined.

(1) Modified RNA Aptamers

Fluorinated RNA aptamers consisting of the same base sequences as the RNA aptamers shown in Example 6 were synthesized using the 2'-fluoro-CTP and the 2'-fluoro-UTP. In the base sequences of the respective fluorinated RNA aptamers, the cytosine nucleotide residues and the uracil nucleotide residues were fluorinated.

The binding ability of each of the RNA aptamers to the rec-cMet was examined in the same manner as in Example 5, except that the fluorinated RNA aptamers were used. The concentration of the rec-cMet was set to 60 nmol/L. With the time point at which the introduction of the rec-cMet to the chip was started being 0 seconds, introduction of a buffer was started 60 seconds later. As a comparative example, the same negative control as in Example 6 was used.

Figure 12:
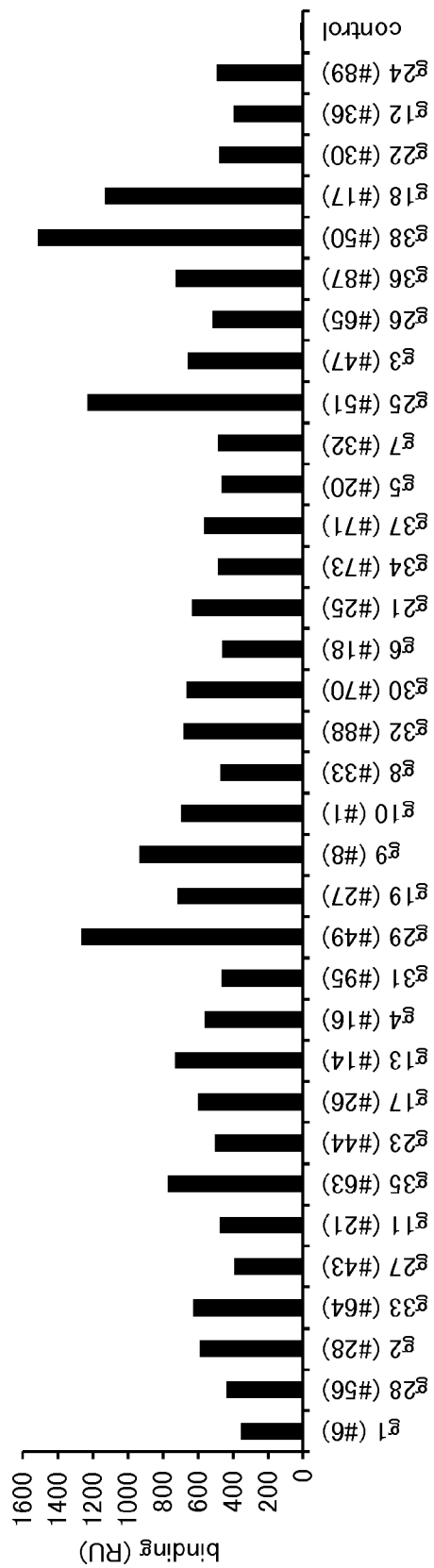
FIG. 12 is a graph showing the binding ability of each RNA aptamer to the recombinant c-Met in Example 7 of the present invention.

The results thereof are shown in FIG. 12. FIG. 12 is a graph showing the binding ability of each of the RNA aptamers to the rec-cMet. In FIG. 12, the vertical axis indicates the signal intensity (RU) measured with BIACORE (registered trademark) X. The signal intensity shown in the graph is a value measured at the 60th second when the buffer was introduced. As shown in FIG. 12, the RNA aptamers all exhibited a binding force. In particular, the fluorinated RNA aptamers g29 (#49), g38 (#50), and g25 (#51) (among them, especially the fluorinated RNA aptamer g38 (#50)) exhibited an excellent binding ability. By fluorination, these RNA aptamers had acquired RNase resistance and they also maintained the bonding force to the c-Met. Thus, it can be seen that these fluorinated RNA aptamers are particularly suitable for use in vivo and in vitro. All the RNA aptamers maintained equivalent signal values subsequent to the 60th second. Thus, it was confirmed that no decrease in binding ability occurred.

Example 8

The influence of a modified RNA aptamer on cell movement was examined.

(1) Modified RNA aptamer

A fluorinated RNA aptamer consisting of the base sequence of g38 (#50) was synthesized using the 2'-fluoro-CTP and the 2'-fluoro-UTP in the same manner as in Example 7. In the base sequence of the fluorinated RNA aptamer, the cytosine nucleotide residues and the uracil nucleotide residues were fluorinated.

(2) Examination of Cell Movement

Using a commercially available cell culture insert (trade name: "Cell Culture Insert", BD Falcon) in accordance with its instructions for use, cell movement of a human glioma cell-derived T98G cell line was examined. Specifically, first, the T98G cell line was cultured at 37° C. for 48 hours in oligotrophic conditions using a 0.1% BSA-containing serum-free medium. Then, the medium was placed in a lower part of the insert, and the cultured T98G cell line was inoculated on the membrane (pore size: 8 µm) of the insert and cultured at 37° C. for 16 hours. After the culture, the number of cells that had passed through the membrane to reach the back side of the membrane was counted. As the medium, a 0.1% BSA-containing serum-free medium (HGF+modified g38) containing 50 ng/mL HGF and the 1 µg/mL modified RNA aptamer was used. As a comparative example, a medium (HGF) containing the HGF only and a medium (HGF+control) containing the HGF and 1 µg/mL control RNA were used. As a control, a medium (−) free of the HGF and the modified RNA aptamer was used. As the control RNA, the same negative control RNA as in Example 6 was used.

Figure 13:
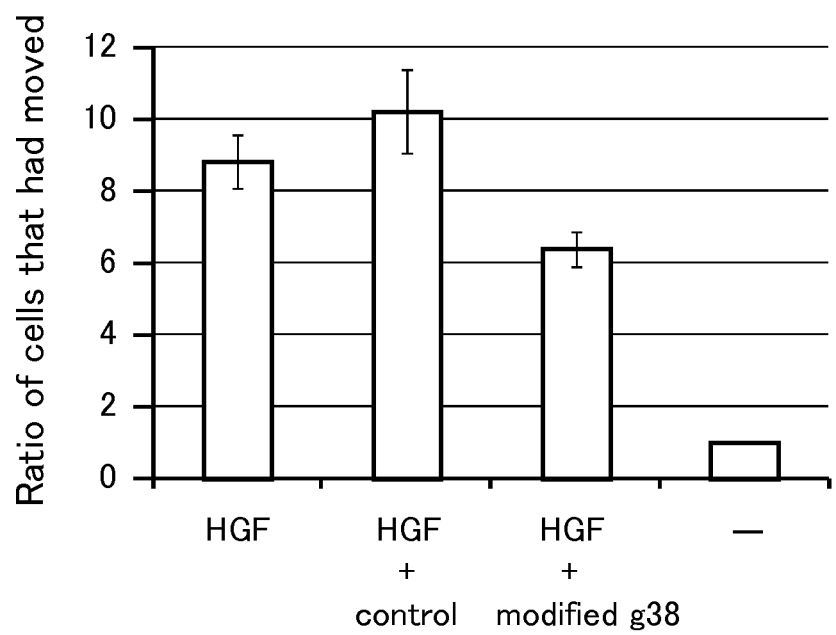
FIG. 13 is a graph showing the ratio of cells that had moved in the presence of an RNA aptamer in Example 8 of the present invention.

The results thereof are shown in FIG. 13. FIG. 13 is a graph showing the movement of the T98G cell line in the presence of the modified RNA, and the vertical axis indicates the ratio of the number of cells that had passed through the membrane to reach the back side of the membrane. The ratio was calculated assuming that the number of cells that had moved in the medium (−) free of the HGF and the modified RNA aptamer was 1.

As shown in FIG. 13, cell movement was hardly observed in the HGF free medium (−), whereas cell movement was promoted in the medium (HGF) containing HGF. In contrast, in the medium (HGF+modified g38) containing the modified RNA aptamers, cell movement was inhibited. In the case where the negative control RNA was added (HGF+control), cell movement was not inhibited. As seen from the above, in the cell culture insert that provides conditions equivalent to those in vivo, cell movement was inhibited by adding the modified RNA aptamer. This demonstrates that the RNA aptamer according to the present invention can inhibit cell movement and cell infiltration also in vivo.

While the present invention has been described above with reference to illustrative embodiments, the present invention is by no means limited thereto. Various changes and modifications that may become apparent to those skilled in the art may be made in the configuration and specifics of the present invention without departing from the scope of the present invention.

This application claims priority from Japanese Patent Application No. 2010-167342 filed on Jul. 26, 2010. The entire disclosure of this Japanese patent application is incorporated herein by reference.

INDUSTRIAL APPLICABILITY

The c-Met binding nucleic acid molecule of the present invention can bind to c-Met. Thus, the c-Met binding nucleic acid molecule of the present invention inhibits the function of c-Met by binding thereto, thereby allowing the prevention and treatment of the above-described diseases caused by c-Met, for example. Furthermore, according to the c-Met binding nucleic acid molecule of the present invention, it is possible to detect c-Met by checking the presence or absence of the binding thereof with the c-Met, for example. Thus, the c-Met binding nucleic acid molecule of the present invention also allows early diagnosis of the above-described diseases. Moreover, the c-Met binding nucleic acid molecule of the present invention can be used for clarification of the function of c-Met, because, for example, experiments involving inhibition of gene transcription become possible by causing the c-Met binding nucleic acid molecule of the present invention to be expressed in cultured cells and also experiments involving inhibition of the binding of extracellular c-Met with its receptor become possible by using the c-Met binding nucleic acid molecule of the present invention. Thus, the c-Met binding nucleic acid molecule of the present invention is useful also as a novel tool for research.

[Sequence Listing]

The invention claimed is:

1. A nucleic acid aptamer molecule that binds to c-Met, wherein said aptamer molecule consists of the sequence of SEQ ID NO: 76.

2. The aptamer molecule according to claim 1, wherein the aptamer molecule contains at least one modified nucleotide.

3. The aptamer molecule according to claim 2, wherein said at least one modified nucleotide is selected from the group consisting of a methylated nucleotide, a fluorinated nucleotide, an aminated nucleotide, and a thiated nucleotide.

4. The aptamer molecule according to claim 2, wherein said at least one modified nucleotide is a modified cytosine or modified uracil.

5. The aptamer molecule according to claim 2, wherein said at least one modified nucleotide is a nucleotide with a modified ribose residue.

6. A neutralizer comprising:
the aptamer molecule according to claim 1,
wherein the neutralizer neutralizes the function of a c-Met protein by binding of the aptamer molecule to the c-Met protein.

7. An inhibitor comprising:
the aptamer molecule according to claim 1,
wherein the inhibitor inhibits the function of a c-Met protein by binding of the aptamer molecule to the c-Met protein.

8. A pharmaceutical agent comprising:
the aptamer molecule according to claim 1.

9. The pharmaceutical agent according to claim 8, wherein the pharmaceutical agent is selected from the group consisting of anticancer agents, antiinflammatory agents, antihepatopathy agents, and anti-amyotrophic lateral sclerosis agents.

10. A composition comprising:
the aptamer molecule according to claim 1.

11. The composition according to claim 10, further comprising a carrier.

12. A c-Met detection reagent for detecting a c-Met protein, wherein the c-Met detection reagent comprises the aptamer molecule according to claim 1.

* * * * *

UNITED STATES PATENT AND TRADEMARK OFFICE
CERTIFICATE OF CORRECTION

PATENT NO.         : 8,822,667 B2                                Page 1 of 1
APPLICATION NO.    : 13/812190
DATED              : September 2, 2014
INVENTOR(S)        : Naomi Hirabayashi et al.

It is certified that error appears in the above-identified patent and that said Letters Patent is hereby corrected as shown below:

In the Specification

Column 15, Line 4: delete "u100de1" and insert -- u10de1 --

Signed and Sealed this
Seventeenth Day of February, 2015

Michelle K. Lee
*Deputy Director of the United States Patent and Trademark Office*